US012685607B2

(12) United States Patent
Ke et al.

(10) Patent No.: US 12,685,607 B2
(45) Date of Patent: Jul. 21, 2026

(54) TISSUE PROTECTION SYSTEMS AND METHODS

(71) Applicant: PROCEPT BioRobotics Corporation, San Jose, CA (US)

(72) Inventors: Qingxiang Ke, San Jose, CA (US); Peter Bentley, Reno, NV (US); Nishey Wanchoo, San Mateo, CA (US)

(73) Assignee: PROCEPT BioRobotics Corporation, San Jose, CA (US)

( * ) Notice: Subject to any disclaimer, the term of this patent is extended or adjusted under 35 U.S.C. 154(b) by 442 days.

(21) Appl. No.: 18/163,164

(22) Filed: Feb. 1, 2023

(65) Prior Publication Data

US 2024/0252271 A1     Aug. 1, 2024

(51) Int. Cl.
*A61B 90/00*          (2016.01)
*A61B 34/10*          (2016.01)
*A61B 18/00*          (2006.01)

(52) U.S. Cl.
CPC .............. *A61B 90/04* (2016.02); *A61B 34/10* (2016.02); *A61B 2018/00547* (2013.01); *A61B 2018/00601* (2013.01); *A61B 2018/00702* (2013.01); *A61B 2018/00994* (2013.01); *A61B 2034/104* (2016.02)

(58) Field of Classification Search
CPC ... A61B 90/04; A61B 34/10; A61B 2034/104; A61B 2018/00547; A61B 2018/00601; A61B 2018/00702; A61B 2018/00994
See application file for complete search history.

(56) References Cited

U.S. PATENT DOCUMENTS

| | | | |
|---|---|---|---|
| 8,152,816 | B2 | 4/2012 | Tuma |
| 8,229,188 | B2 | 7/2012 | Rusko |
| 9,144,461 | B2 | 9/2015 | Kruecker |
| 9,277,969 | B2 | 3/2016 | Brannan |

(Continued)

FOREIGN PATENT DOCUMENTS

| | | |
|---|---|---|
| CN | 113633372 | 11/2021 |
| CN | 113796952 | 12/2021 |

(Continued)

OTHER PUBLICATIONS

Co-pending U.S. Appl. No. 18/163,187, filed Feb. 1, 2023.

(Continued)

*Primary Examiner* — Patricia J Park
(74) *Attorney, Agent, or Firm* — Knobbe, Martens, Olson & Bear, LLP

(57)          ABSTRACT

A probe configured to deliver energy to a first tissue is placed in the first tissue, and an imaging device is configured to image a second tissue with the probe placed in the first tissue. Image data from the second tissue is processed to evaluate the effect of the energy source on the second tissue. In some embodiments, the image data from the second tissue is used to adjust the energy to the first tissue, for example by increasing or decreasing the energy to the second tissue. In some embodiments, image data from the first tissue or the second tissue or force sensor data from the probe is used to evaluate placement of the probe in the first tissue, and the placement of the probe in the first tissue adjusted to decrease tissue alterations of the second tissue related to probe placement in the first tissue.

21 Claims, 16 Drawing Sheets

1100

| | |
|---|---|
| insert treatment probe into patient to treat first tissue | 1105 |
| position imaging device to image second tissue and first tissue | 1110 |
| image first tissue and second tissue | 1115 |
| identify tissue structures of first tissue and associated data | 1120 |
| identify tissue structures of second tissue and associated data | 1125 |
| generate three dimensional treatment profile | 1130 |
| output three dimensional profile to display of user interface overlaid on associated images | 1135 |
| adjust three dimensional treatment profile in response to user input | 1140 |
| direct energy from energy source to treat first tissue | 1145 |
| image first tissue while energy source treats first tissue | 1150 |
| process image data from image of first tissue | 1155 |
| image second tissue while energy source treats first tissue | 1160 |
| process image data from image of second tissue acquired when first tissue treated | 1165 |
| determine response of second tissue to treatment of first tissue | 1170 |
| correlate treatment of first tissue with movement of second tissue | 1175 |
| output data corresponding to response of second tissue to treatment of first tissue | 1180 |
| output data from second tissue to user interface | 1185 |
| receive user input from user interface related to second tissue output data | 1190 |
| adjust treatment of first tissue based on response of second tissue to treatment of first tissue | 1195 |
| treat first tissue with adjusted treatment | 1199 |

(56) References Cited

U.S. PATENT DOCUMENTS

| | | | |
|---|---|---|---|
| 10,226,298 | B2 | 3/2019 | Ourselin |
| 10,423,757 | B2 | 9/2019 | Kruecker |
| 10,448,956 | B2 | 10/2019 | Gordon |
| 11,278,451 | B2 | 3/2022 | Andrews |
| 2008/0027420 | A1 | 1/2008 | Wang |
| 2011/0299750 | A1 | 12/2011 | Cool |
| 2012/0130241 | A1 | 5/2012 | Wang |
| 2015/0016682 | A1* | 1/2015 | Levy ..................... A61N 7/02 |
| | | | 382/103 |
| 2016/0256225 | A1 | 9/2016 | Crawford |
| 2016/0332005 | A1 | 11/2016 | Fedewa |
| 2017/0273797 | A1 | 9/2017 | Gordon |
| 2017/0333137 | A1 | 11/2017 | Roessler |
| 2018/0028261 | A1 | 2/2018 | Chen |
| 2018/0318011 | A1 | 11/2018 | Leibinger |
| 2019/0000319 | A1 | 1/2019 | Mak |
| 2019/0064290 | A1 | 2/2019 | Bailey |
| 2019/0069962 | A1 | 3/2019 | Tabandeh |
| 2019/0201214 | A1 | 7/2019 | Miller |
| 2020/0360100 | A1 | 11/2020 | Mantri |
| 2020/0375622 | A1 | 12/2020 | Aljuri |
| 2021/0121251 | A1* | 4/2021 | Aljuri ................... G16H 20/40 |
| 2022/0133331 | A1 | 5/2022 | Abbasi |
| 2022/0241037 | A1 | 8/2022 | Crawford |
| 2022/0241981 | A1 | 8/2022 | Fredrickson |
| 2022/0288424 | A1* | 9/2022 | Vortman .................. A61N 7/02 |
| 2023/0414299 | A1* | 12/2023 | Khuri-Yakub ....... A61B 8/4494 |
| 2024/0252845 | A1* | 8/2024 | Khuri-Yakub ......... G16H 50/20 |
| 2024/0285346 | A1 | 8/2024 | Shi |
| 2024/0299003 | A1 | 9/2024 | Shi |

FOREIGN PATENT DOCUMENTS

| | | | |
|---|---|---|---|
| CN | 113940753 | | 1/2022 |
| CN | 113951935 | | 1/2022 |
| CN | 114145781 | | 3/2022 |
| CN | 114320879 | | 4/2022 |
| CN | 114376610 | | 4/2022 |
| CN | 114521939 | | 5/2022 |
| CN | 216495529 | | 5/2022 |
| CN | 216675776 | | 6/2022 |
| CN | 216675785 | | 6/2022 |
| CN | 217338655 | | 9/2022 |
| CN | 115607282 | | 1/2023 |
| CN | 115634042 | | 1/2023 |
| CN | 115955052 | | 4/2023 |
| EP | 1486900 | | 12/2004 |
| KR | 101869826 | | 6/2018 |
| WO | 2008083407 | | 7/2008 |
| WO | 2009111736 | | 9/2009 |
| WO | 2011097505 | | 8/2011 |
| WO | 2011097505 | A1 | 8/2011 |
| WO | 2013053614 | | 4/2013 |
| WO | 2013130895 | | 9/2013 |
| WO | 2013130895 | A1 | 9/2013 |
| WO | 2014127242 | | 8/2014 |
| WO | 2014127242 | A2 | 8/2014 |
| WO | 2014165703 | | 10/2014 |
| WO | 2014165703 | A1 | 10/2014 |
| WO | 2015035249 | | 3/2015 |
| WO | 2015035249 | A2 | 3/2015 |
| WO | 2015200538 | | 12/2015 |
| WO | 2015200538 | A1 | 12/2015 |
| WO | 2016004071 | | 1/2016 |
| WO | 2016004071 | A1 | 1/2016 |
| WO | 2016037132 | | 3/2016 |
| WO | 2016037132 | A1 | 3/2016 |
| WO | 2016037137 | | 3/2016 |
| WO | 2016037137 | A1 | 3/2016 |
| WO | 2017161331 | | 9/2017 |
| WO | 2017161331 | A1 | 9/2017 |
| WO | 2019032986 | | 2/2019 |
| WO | 2019137665 | | 7/2019 |
| WO | 2019246580 | | 12/2019 |
| WO | 2020180724 | | 9/2020 |
| WO | 2020181278 | | 9/2020 |
| WO | 2020181280 | | 9/2020 |
| WO | 2020181281 | | 9/2020 |
| WO | 2020181290 | | 9/2020 |
| WO | 2021096741 | | 5/2021 |
| WO | 2021262565 | | 12/2021 |
| WO | 2021263276 | | 12/2021 |
| WO | 2022006248 | | 1/2022 |
| WO | 2022011177 | | 1/2022 |
| WO | 2022226103 | | 10/2022 |
| WO | 2023066148 | | 4/2023 |
| WO | 2023072146 | | 5/2023 |
| WO | 2023083352 | | 5/2023 |
| WO | 2023088305 | | 5/2023 |
| WO | 2023159096 | | 8/2023 |
| WO | 2023159101 | | 8/2023 |
| WO | 2023179756 | | 9/2023 |
| WO | 2023207917 | | 11/2023 |
| WO | 2024114841 | | 6/2024 |
| WO | 2024140703 | | 7/2024 |

OTHER PUBLICATIONS

Garnica-Garza, HM. Directional scatter imaging for the stereoscopic tracking of fiducial markers in a single kV exposure. Med Phys. Feb. 2018;45(2):703-713. doi: 10.1002/mp.12712. Epub Dec. 21, 2017. PMID: 29206280.

Košťák M, Slabý A. Designing a Simple Fiducial Marker for Localization in Spatial Scenes Using Neural Networks. Sensors (Basel). Aug. 10, 2021;21(16):5407. doi: 10.3390/s21165407. PMID: 34450848; PMCID: PMC8400176.

Stathakis, Alexandros, "Vision-Based Localization using Reliable Fiducial Markers," retrieved from https://citeseerx.ist.psu.edu/viewdoc/download?doi=10.1.1.895.3616&rep=rep1&type=pdf (Dec. 2011).

International Search Report and Written Opinion for PCT/US2024/013458, 21 pages (Jun. 13, 2024).

* cited by examiner

Perspective view

Sagittal view

Superior view

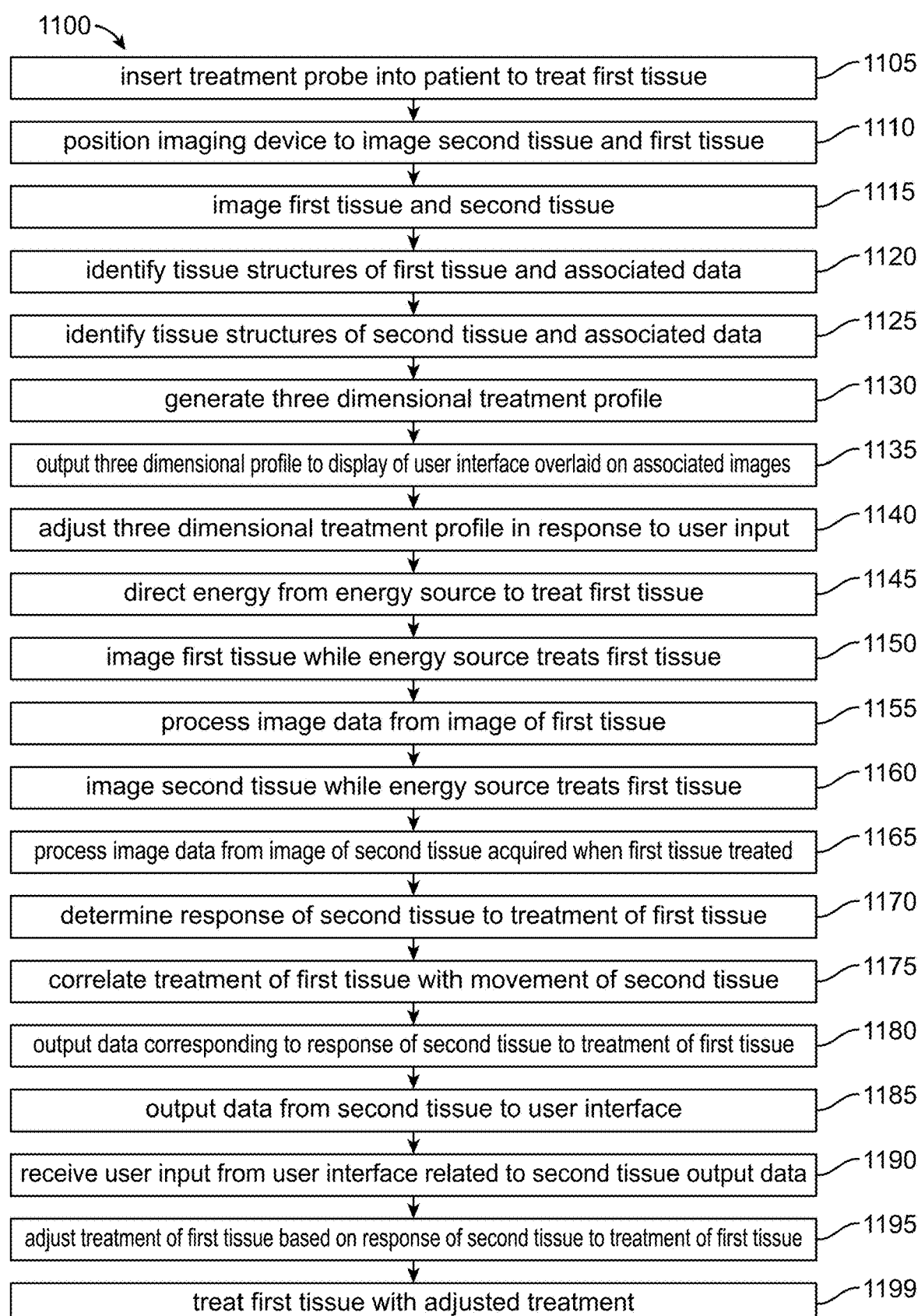

1100 insert treatment probe into patient to treat first tissue — 1105 position imaging device to image second tissue and first tissue — 1110 image first tissue and second tissue — 1115 identify tissue structures of first tissue and associated data — 1120 identify tissue structures of second tissue and associated data — 1125 generate three dimensional treatment profile — 1130 output three dimensional profile to display of user interface overlaid on associated images — 1135 adjust three dimensional treatment profile in response to user input — 1140 direct energy from energy source to treat first tissue — 1145 image first tissue while energy source treats first tissue — 1150 process image data from image of first tissue — 1155 image second tissue while energy source treats first tissue — 1160 process image data from image of second tissue acquired when first tissue treated — 1165 determine response of second tissue to treatment of first tissue — 1170 correlate treatment of first tissue with movement of second tissue — 1175 output data corresponding to response of second tissue to treatment of first tissue — 1180 output data from second tissue to user interface — 1185 receive user input from user interface related to second tissue output data — 1190 adjust treatment of first tissue based on response of second tissue to treatment of first tissue — 1195 treat first tissue with adjusted treatment — 1199

FIG. 11

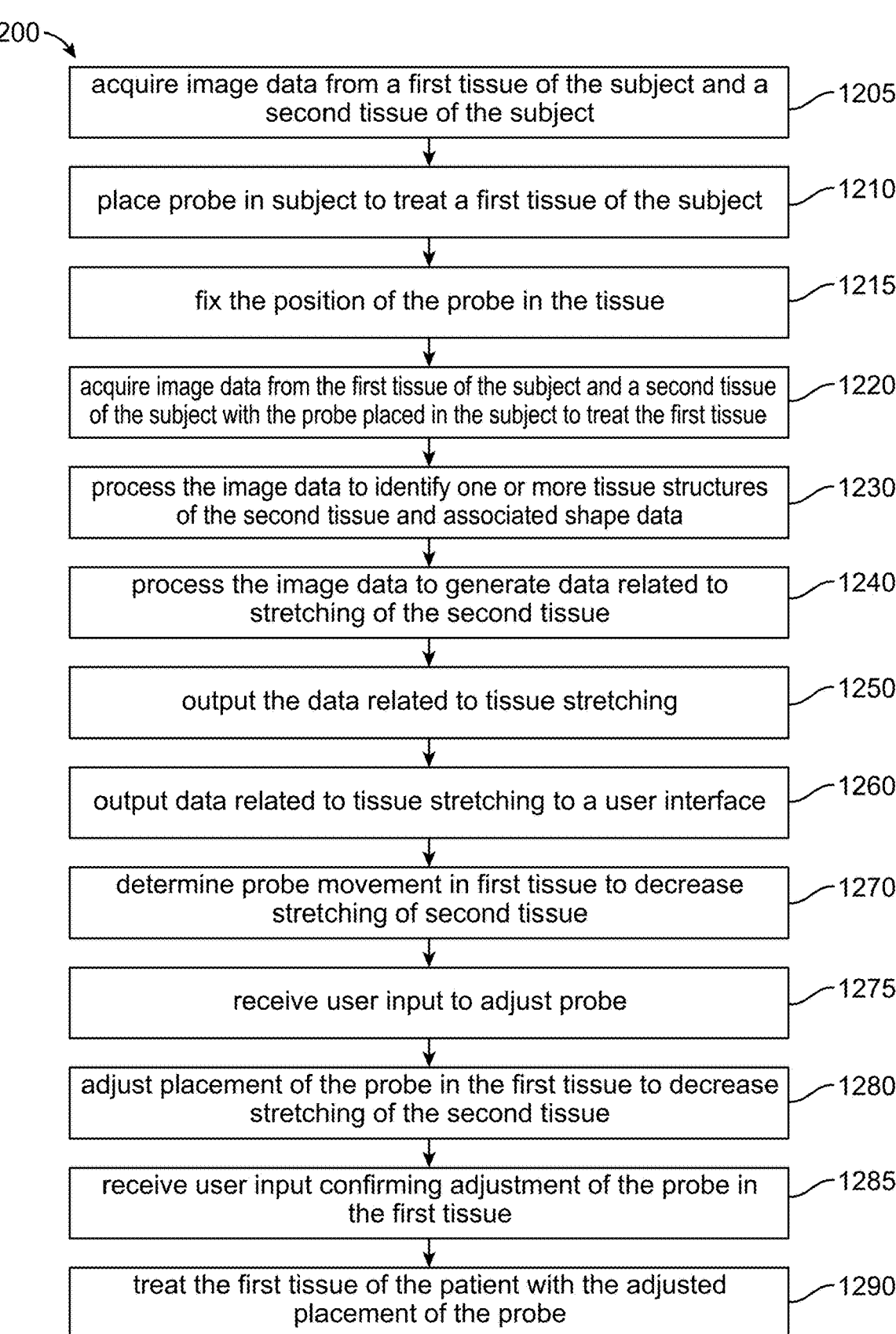

1200 acquire image data from a first tissue of the subject and a second tissue of the subject ⌐1205 place probe in subject to treat a first tissue of the subject ⌐1210 fix the position of the probe in the tissue ⌐1215 acquire image data from the first tissue of the subject and a second tissue of the subject with the probe placed in the subject to treat the first tissue ⌐1220 process the image data to identify one or more tissue structures of the second tissue and associated shape data ⌐1230 process the image data to generate data related to stretching of the second tissue ⌐1240 output the data related to tissue stretching ⌐1250 output data related to tissue stretching to a user interface ⌐1260 determine probe movement in first tissue to decrease stretching of second tissue ⌐1270 receive user input to adjust probe ⌐1275 adjust placement of the probe in the first tissue to decrease stretching of the second tissue ⌐1280 receive user input confirming adjustment of the probe in the first tissue ⌐1285 treat the first tissue of the patient with the adjusted placement of the probe ⌐1290

FIG. 12

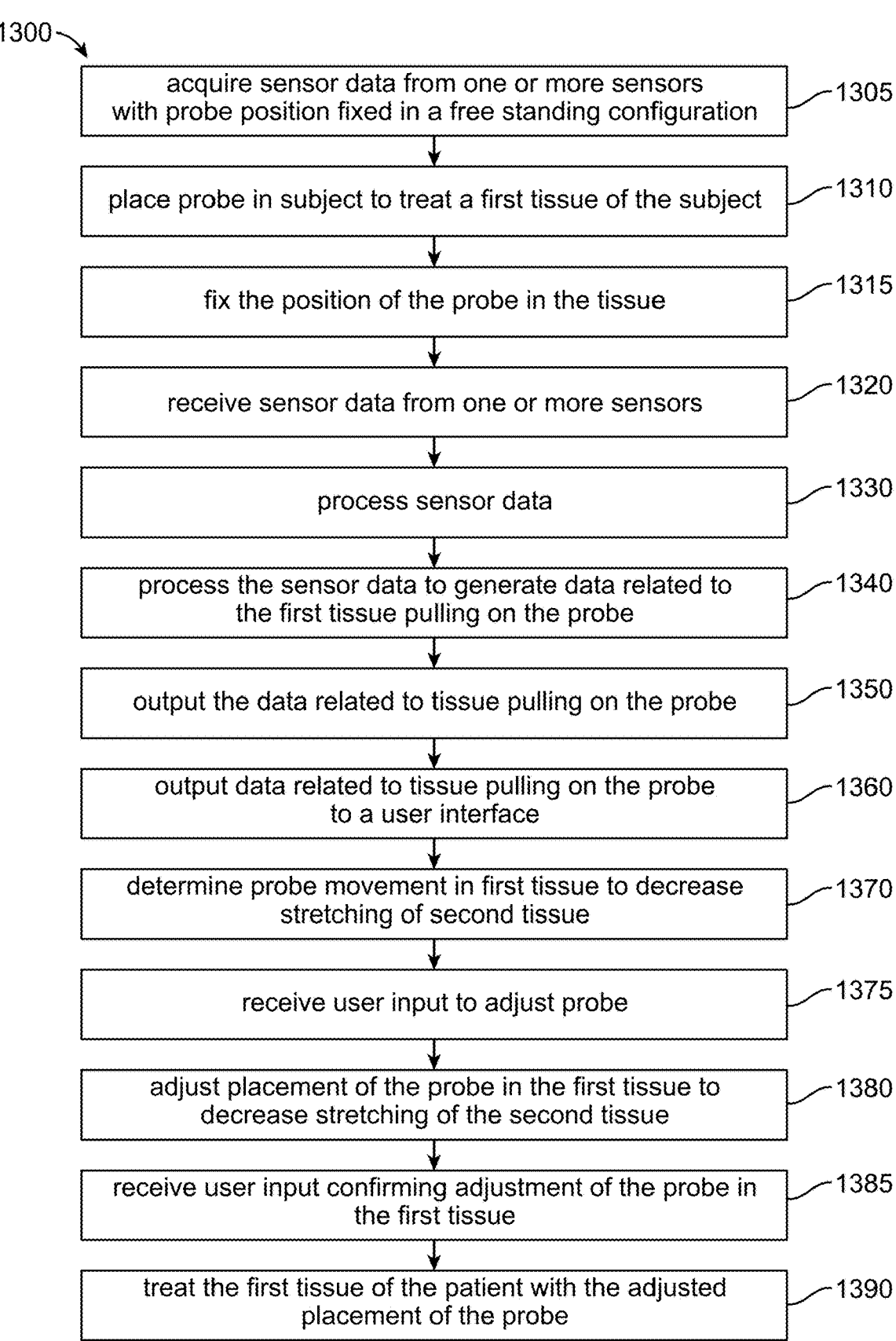

1300 acquire sensor data from one or more sensors with probe position fixed in a free standing configuration ⟋1305 place probe in subject to treat a first tissue of the subject ⟋1310 fix the position of the probe in the tissue ⟋1315 receive sensor data from one or more sensors ⟋1320 process sensor data ⟋1330 process the sensor data to generate data related to the first tissue pulling on the probe ⟋1340 output the data related to tissue pulling on the probe ⟋1350 output data related to tissue pulling on the probe to a user interface ⟋1360 determine probe movement in first tissue to decrease stretching of second tissue ⟋1370 receive user input to adjust probe ⟋1375 adjust placement of the probe in the first tissue to decrease stretching of the second tissue ⟋1380 receive user input confirming adjustment of the probe in the first tissue ⟋1385 treat the first tissue of the patient with the adjusted placement of the probe ⟋1390

FIG. 13

TISSUE PROTECTION SYSTEMS AND METHODS

BACKGROUND

Prior approaches to tissue resection with an energy source can be less than ideal in at least some respects. Work in relation to the present disclosure suggests that prior approaches to treating a first tissue with an energy source may have an undesirable effect on a second tissue. For example, although some types of energy may be effective in treating the first tissue, the energy treating the first tissue may have a collateral effect on the second tissue that may at least partially decrease the functionality of the second tissue. Also, in some instances the treatment of tissue of a first organ may have a collateral effect on a second organ.

This collateral effect can occur in many ways, such as undesirable amounts of energy, or less than ideal alignment of a probe with a tissue structure. Probes can be used to treat many types of tissue and organs, and work in relation to the present disclosure suggests that misalignment of a probe can result in unintended effects to tissue that is spaced apart from the probe. Also, if the treated tissue reacts in an unpredictable way, then an energy source has the potential to have a collateral effect on a second tissue in at least some instances. For example, with prostate tissue surgery, the verumontanum and the trigone region of the bladder are tissue structures that can be potentially altered during surgery with undesirable consequences in at least some instances. The trigone region of the bladder is sensitive to stretching and transmits signals to the brain to empty the bladder. However, damage to the trigone region can create the sensation that the bladder should be emptied even when this is not case, which can result in patient discomfort in some instances. The verumontanum of the prostate is related to sexual function, and damage to the verumontanum can result in decreased sexual function in males in at least some instances.

In light of the above, it would be desirable to have improved surgical systems and methods that ameliorate at least some of the aforementioned limitations of the prior art.

SUMMARY

The presently disclosed systems and methods provide improved treatment of tissue with an energy source while decreasing potentially undesirable effects on other tissue. In some embodiments, a probe is configured to deliver energy to a first tissue, and an imaging device is configured to image a second tissue. Image data from the second tissue is processed to evaluate the effect of the energy source on the second tissue. In some embodiments, the image data from the second tissue is used to adjust the energy to the first tissue, for example by increasing or decreasing the energy to the second tissue. In some embodiments, image data from one or more of the first tissue or the second tissue is used to evaluate placement of the probe in the first tissue, and the placement of the probe in the first tissue adjusted to decrease tissue alterations of the second tissue related to probe placement in the first tissue. In some embodiments, the probe is coupled to force sensors to measure tissue pulling on the probe, which can decrease potentially undesirable effects to the second tissue.

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 11 shows a method of treating a first tissue and adjusting the treatment based on a response of a second tissue to the treatment of the first tissue, in accordance with some embodiments;

FIG. 12 shows a method of adjusting a probe placed in a first tissue in response to stretching of a second tissue, in accordance with some embodiments;

FIG. 13 shows a method of measuring forces related to tissue pulling on a probe and adjusting the probe in response to tissue pulling on the probe, in accordance with some embodiments.

DETAILED DESCRIPTION

Figure 1:
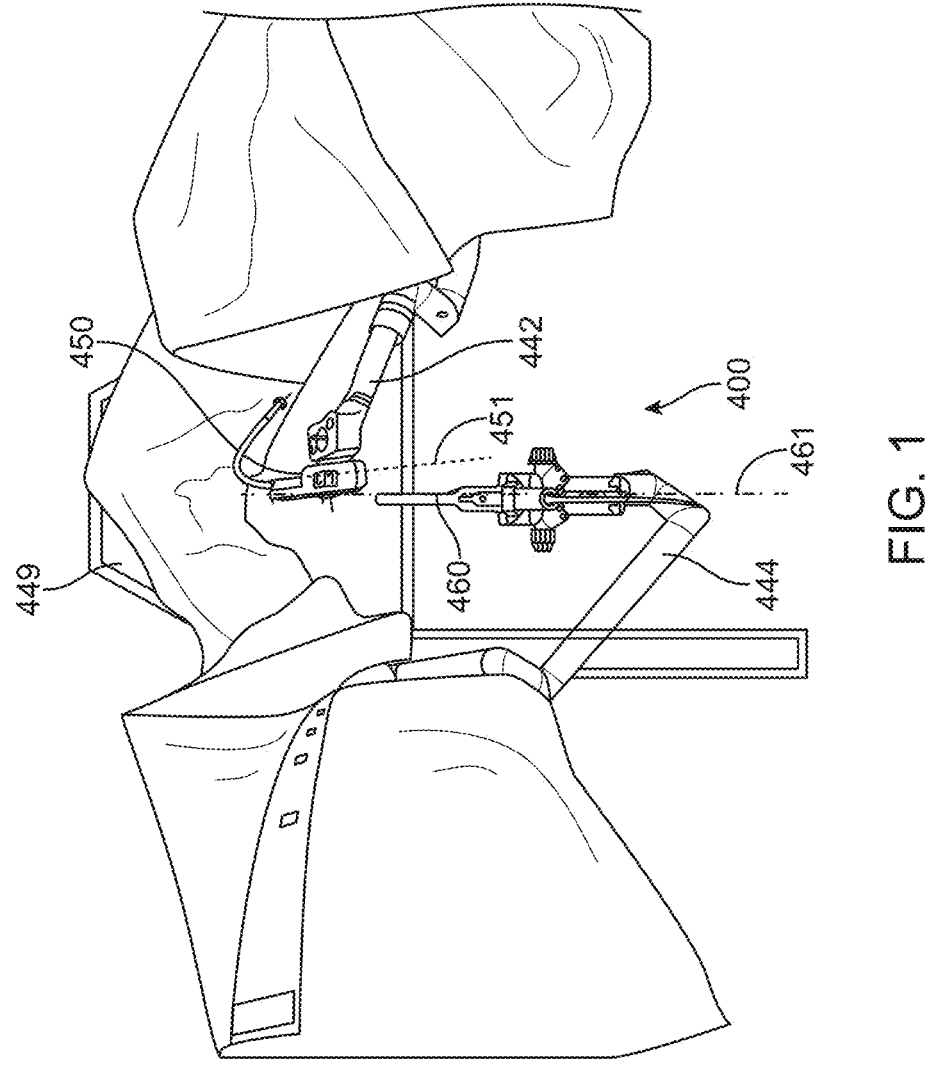
FIG. 1 shows a front view of a system for performing tissue resection in a patient, in accordance with some embodiments of the present disclosure.

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The presently disclosed systems and methods are well suited for use with many probes and diagnostic and surgical procedures. Although reference is made to a treatment probe comprising an energy source for prostate surgery and a transrectal ultrasound ("TRUS") probe, the present disclosure is well suited for use with many types of probes inserted into many types of tissues, organs, cavities and lumens, such as brain, heart, lung, intestinal, eye, skin, kidney, liver, pancreas, stomach, uterus, ovaries, testicles, bladder, ear, nose, mouth, tumors, cancers, soft tissues such as bone marrow, adipose tissue, muscle, glandular and mucosal tissue, spinal and nerve tissue, cartilage, hard biological tissues such as teeth, bone, and lumens such as vascular lumens, nasal lumens and cavities, sinuses, colon, urethral lumens, gastric lumens, airways, esophageal lumens, trans esophageal, intestinal lumens, anal lumens, vaginal lumens, trans abdominal, abdominal cavities, throat, airways, lung passages, and surgery such as kidney surgery, ureter surgery, kidney stones, prostate surgery, tumor surgery, cancer surgery, brain surgery, heart surgery, eye surgery, conjunctival surgery, liver surgery, gall bladder surgery, bladder surgery, spinal surgery, orthopedic surgery, arthroscopic surgery, liposuction, colonoscopy, intubation, minimally invasive incisions, minimally invasive surgery, and others.

The presently disclosed systems and methods are well suited for combination with prior probes such as imaging probes and treatment probes. Examples of such probes include laser treatment probes, water jet probes, RF treatment probes, radiation therapy probes, ultrasound treatment probes, phaco emulsification probes, imaging probes, endoscopic probes, resectoscope probes, ultrasound imaging probes, A-scan ultrasound probes, B-scan ultrasound probes, 3D ultrasound probes, Doppler ultrasound probes, transrectal ultrasound probes, transvaginal ultrasound probes, longitudinal plane ultrasound imaging probes, sagittal plane ultrasound imaging probes, transverse plane ultrasound imaging probes, and transverse and longitudinal plane (e.g. sagittal plane) ultrasound imaging probes, for example.

The one or more images described herein can be generated in many ways, and may comprise one or more of a longitudinal image, a sagittal image, a parasagittal or a transverse image. In some embodiments, a longitudinal image comprises an image generated with an elongate imaging probe, in which the longitudinal image extends along a plane corresponding to an elongate axis of the imaging probe, and the transverse images extend along a plane that is transverse to the elongate axis of the probe, for example substantially perpendicular to the elongate axis of the probe and the corresponding longitudinal images. The elongate probe can be inserted into the patient with any suitable orientation. In some embodiments, the probe is inserted into the patient substantially along a midline of the patient, such that the longitudinal images correspond to sagittal images of the patient. In some embodiments, the elongate imaging probe comprises a TRUS probe, and the longitudinal images comprise sagittal images, although other probes with different orientations can be used to generate images in accordance with the present disclosure. Although reference is made to ultrasound probes inserted into the patient, in some embodiments the imaging device comprises an external imaging probe in which the longitudinal and transverse images can be referenced to one or more arrays of the external imaging probe. In some embodiments, the one or more images are generated from a 3D tomographic image data set such as a Digital Imaging and Communications in Medicine (DICOM) image data set.

The presently disclosed systems, methods and apparatuses are well suited for combination with many prior surgical procedures, such as water jet enucleation of the prostate, transurethral resection of the prostate (TURP), holmium laser enucleation of the prostate (HOLEP), prostate brachytherapy, and with surgical robotics systems and automated surgical procedures. The following patent applications describe examples of systems, methods, probes and procedures suitable for incorporation in accordance with the present disclosure: PCT/US2013/028441, filed Feb. 28, 2013, entitled "AUTOMATED IMAGE-GUIDED TISSUE RESECTION AND TREATMENT, published as WO 2013/130895; PCT/US2014/054412, filed Sep. 5, 2014, entitled "AUTOMATED IMAGE-GUIDED TISSUE RESECTION AND TREATMENT", published as WO 2015/035249; PCT/US2015/048695, filed Sep. 5, 2015, entitled "PHYSICIAN CONTROLLED TISSUE RESECTION INTEGRATED WITH TREATMENT MAPPING OF TARGET ORGAN IMAGES", published as WO2016037137; PCT/US2019/038574, filed Jun. 21, 2019, entitled "ARTIFICIAL INTELLIGENCE FOR ROBOTIC SURGERY", published as WO2019246580A1 on Dec. 26, 2019; PCT/US2020/021756, filed Mar. 9, 2020, entitled "ROBOTIC ARMS AND METHODS FOR TISSUE RESECTION AND IMAGING", published as WO/2020/181290; PCT/US2020/058884, filed on Nov. 4, 2020, entitled "SURGICAL PROBES FOR TISSUE RESECTION WITH ROBOTIC ARMS", published as WO/2021/096741; PCT/US2021/070760, filed on Jun. 23, 2021, entitled "INTEGRATION OF ROBOTIC ARMS WITH SURGICAL PROBES", published as WO/2021/263276; and PCT/US2021/038175, filed on Jun. 21, 2021, entitled "SYSTEMS AND METHODS FOR DEFINING AND MODIFYING RANGE OF MOTION OF PROBE USED IN PATIENT TREATMENT", published as WO/2021/262565; the entire disclosures of which are incorporated herein by reference.

In some embodiments, improved positional accuracy is provided for placement of an energy source. The energy source may comprise any suitable energy source, such as one or more of an electrode, a loop electrode, a laser source, a thermal energy source, a mechanical energy source, a mechanical sheer, an ultrasound probe, a cavitating ultrasound probe, a water jet, e.g. a fixed pressure water jet, a plasma source, a steam source, a morcellator, a trans urethral needle, a photo ablation source, a radiation energy source, a microwave energy source or a water jet evacuation source. The energy source can be combined with other treatments and compounds, such as photochemical treatment agents. The imaging probe may comprise any suitable probe, such as endoscopic probes, resectoscope probes, ultrasound imaging probes, A-scan ultrasound probes, B-scan ultrasound probes, Doppler ultrasound probes, transrectal ultrasound probes, transvaginal ultrasound probes, sagittal plane ultrasound imaging probes, transverse plane ultrasound imaging probes, and transverse and sagittal plane ultrasound imaging probes, for example.

FIG. 1 shows an exemplary embodiment of a system 400 for performing treatment of a patient. The system 400 may comprise a treatment probe 450 as described herein and an imaging probe 460 as described herein. The treatment probe 450 may be coupled to a first arm 442, and the imaging probe 460 coupled to a second arm 444. One or both of the first arm 442 and the second arm 444 may comprise robotic arms whose movements may be controlled by one or more computing devices operably coupled with the arms. The treatment probe 450 may comprise a device for removing target tissue from a target site within a patient. The treatment probe 450 may be configured to deliver energy from the treatment probe 450 to the target tissue sufficient for removing the target tissue, and the energy source may comprise any suitable energy source as describe herein. For example, the treatment probe 450 may comprise an electrosurgical ablation device, a laser ablation device, a transurethral needle ablation device, a water jet ablation device, a steam ablation device, a high-intensity focused ultrasound (HIFU) device, or any combination thereof. The imaging probe 460 may be configured to deliver energy from the imaging probe 460 to the target tissue sufficient for imaging the target tissue. The imaging probe 460 may comprise an ultrasound probe, a magnetic resonance probe, an endoscope, or a fluoroscopy probe, for example. The first arm 442 and the second arm 444 may be configured to be independently adjustable, adjustable according to a fixed relationship, adjustable according to a user selected relationship, independently lockable, or simultaneously lockable, or any combination thereof. The first arm 442 and the second arm 444 may have multiple degrees of freedom, for example six degrees of freedom, to manipulate the treatment probe 450 and the imaging probe 460, respectively. The treatment system 400 may be used to perform tissue resection in an organ of a patient, such a prostate of a patient. The patient may be positioned on a patient support 449 such as a bed, a table, a chair, or a platform. The treatment probe 450 may be inserted into the target site of the patient along an axis of entry that coincides with the elongate axis 451 of the treatment probe. For example, the treatment probe 450 may be configured for insertion into the urethra of the patient, so as to position an energy delivery region of the treatment probe within the prostate of the patient. The imaging probe 460 may be inserted into the patient at the target site or at a site adjacent the target site of the patient, along an axis of entry that coincides with the elongate axis 461 of the imaging probe. For example, the imaging probe 460 may comprise a transrectal ultrasound (TRUS) probe, configured for insertion into the rectum of the patient to view the patient's prostate and the surrounding tissues. As shown in FIG. 1, the first arm 442 and the second arm 444 may be covered in sterile drapes to provide a sterile operating environment, keep the robotic arms clean, and reduce risks of damaging the robotic arms. Further details regarding the various components of the system 400 suitable for incorporation with embodiments as disclosed herein may be found in U.S. Pat. Nos. 7,882,841, 8,814,921, 9,364,251, and PCT Publication No. WO2013/130895, the entire disclosures of which are incorporated herein by reference.

Figure 2:
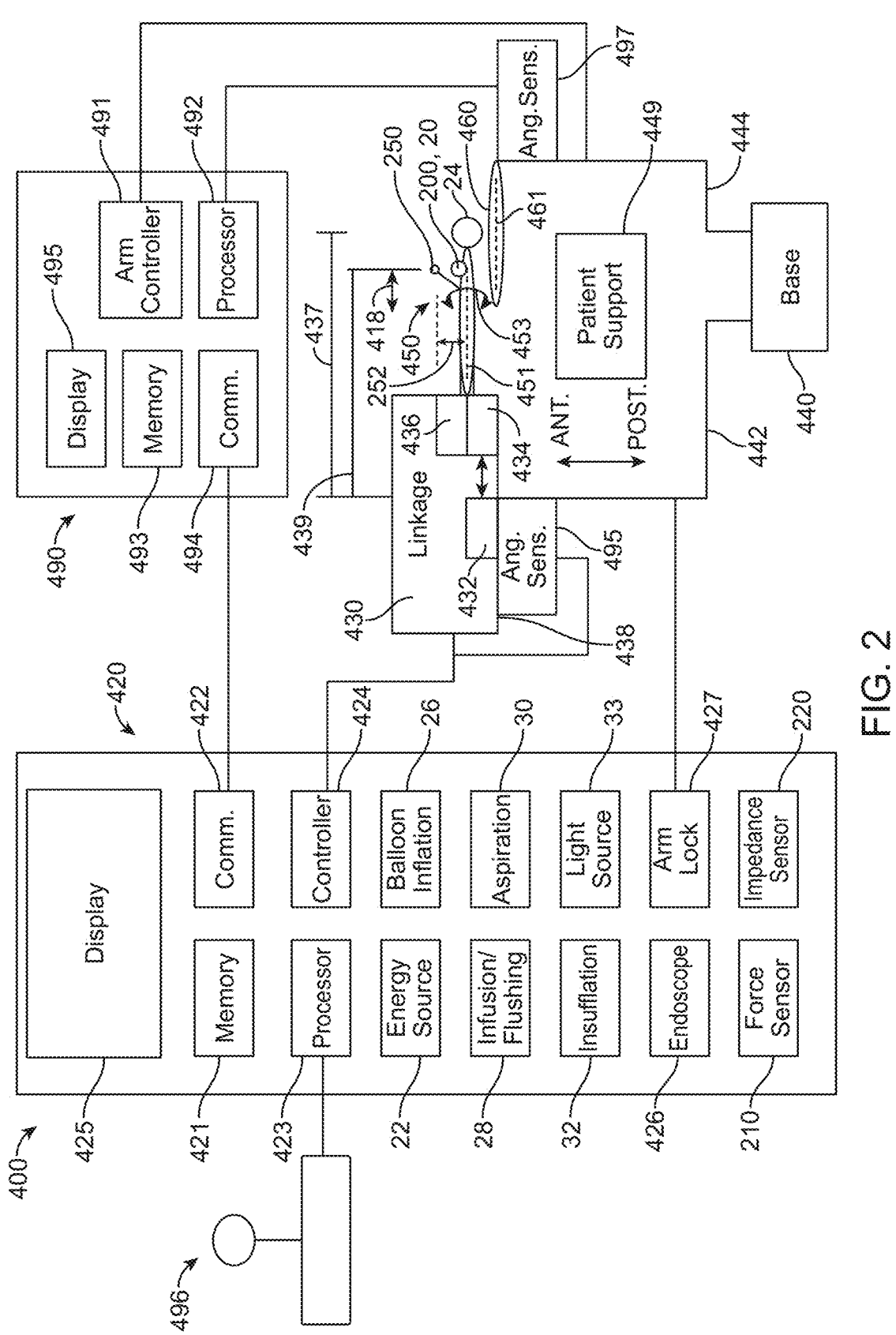
FIG. 2 schematically illustrates a system for performing tissue resection in a patient, in accordance with some embodiments.

FIG. 2 schematically illustrates embodiments of the system 400 for performing tissue resection in a patient. The system 400 may comprise a treatment probe 450 as described herein and may optionally comprise an imaging probe 460. The treatment probe 450 is coupled to a console 420 and a linkage 430. The linkage 430 may comprise one or more components of the robotic arm 442. The imaging probe 460 is coupled to an imaging console 490. The imaging probe may be coupled to the second robotic arm 444, for example. The patient treatment probe 450 and the imaging probe 460 can be coupled to a common base 440. The patient is supported with the patient support 449. The treatment probe 450 is coupled to the base 440 with a first arm 442. The imaging probe 460 is coupled to the base 440 with a second arm 444. One or both of the first arm 442 and the second arm 444 may comprise robotic arms whose movements may be controlled by one or more computing devices operably coupled with the arms, as described in further detail herein.

Although reference is made to a common base, the robotic arms can be coupled to a bed rail, a console, or any suitable supporting structure to support the base of the robotic arm.

In some embodiments, system 400 comprises a user input device 496 coupled to processor 423 for a user to manipulate the surgical instrument on the robotic arm. A user input device 496 can be located in any suitable place, for example, on a console, on a robotic arm, on a mobile base, and there may be one, two, three, four, or more user input devices used in conjunction with the system 400 to either provide redundant avenues of input, unique input commands, or a combination. In some embodiments, the user input device comprises a controller to move the end of the treatment probe or the imaging probe with movements in response to mechanical movements of the user input device. The end of the probe can be shown on the display 425 and the user can manipulate the end of the probe. For example, the user input device may comprise a 6 degree of freedom input controller in which the user is able to move the input device with 6 degrees of freedom, and the distal end of the probe moves in response to movements of the controller. In some embodiments, the 6 degrees of freedom comprise three translational degrees of freedom and three rotational degrees of freedom. The processor can be configured with instructions for the probe control to switch between automated image guidance treatment with the energy source and treatment with the energy source with user movement of the user input device, for example.

The patient is placed on the patient support 449, such that the treatment probe 450 and ultrasound probe 460 can be inserted into the patient. The patient can be placed in one or more of many positions such as prone, supine, upright, or inclined, for example. In some embodiments, the patient is placed in a lithotomy position, and stirrups may be used, for example. In some embodiments, the treatment probe 450 is inserted into the patient in a first direction on a first side of the patient, and the imaging probe is inserted into the patient in a second direction on a second side of the patient. For example, the treatment probe can be inserted from an anterior side of the patient into a urethra of the patient, and the imaging probe can be inserted trans-rectally from a posterior side of the patient into the intestine of the patient. The treatment probe and imaging probe can be placed in the patient with one or more of urethral tissue, urethral wall tissue, prostate tissue, intestinal tissue, or intestinal wall tissue extending therebetween.

The treatment probe 450 and the imaging probe 460 can be inserted into the patient in one or more of many ways. During insertion, each of the first and second arms may comprise a substantially unlocked configuration such the treatment or imaging probe can be desirably rotated and translated in order to insert the probe into the patient. When the probe has been inserted to a desired location, the arm can be locked. In the locked configuration, the probes can be oriented in relation to each other in one or more of many ways, such as parallel, skew, horizontal, oblique, or non-parallel, for example. It can be helpful to determine the orientation of the probes with angle sensors as described herein, in order to map the image date of the imaging probe to treatment probe coordinate references. Having the tissue image data mapped to treatment probe coordinate reference space can allow accurate targeting and treatment of tissue identified for treatment by an operator such as the physician.

In some embodiments, the treatment probe 450 is coupled to the imaging probe 460 in order to align the treatment with probe 450 based on images from imaging probe 460. The coupling can be achieved with the common base 440 as shown. Alternatively or in combination, the treatment probe and/or the imaging probe may comprise magnets to hold the probes in alignment through tissue of the patient. In some embodiments, the first arm 442 is a movable and lockable arm such that the treatment probe 450 can be positioned in a desired location in a patient. When the probe 450 has been positioned in the desired location of the patient, the first arm 442 can be locked with an arm lock 427. The imaging probe can be coupled to base 440 with the second arm 444, which can be used to adjust the alignment of the imaging probe when the treatment probe is locked in position. The second arm 444 may comprise a lockable and movable arm under control of the imaging system or of the console and of the user interface, for example. The movable arm 444 may be micro-actuatable so that the imaging probe 460 can be adjusted with small movements, for example a millimeter or so in relation to the treatment probe 450.

In some embodiments, the treatment probe 450 and the imaging probe 460 are coupled to angle sensors so that the treatment can be controlled based on the alignment of the imaging probe 460 and the treatment probe 450. A first angle sensor 495 may be coupled to the treatment probe 450 with a support 438. A second angle sensor 497 may be coupled to the imaging probe 460. The angle sensors may comprise one or more of many types of angle sensors. For example, the angle sensors may comprise goniometers, accelerometers and combinations thereof. In some embodiments, the first angle sensor 495 comprises a 3-dimensional accelerometer to determine an orientation of the treatment probe 450 in three dimensions. In some embodiments, the second angle sensor 497 comprises a 3-dimensional accelerometer to determine an orientation of the imaging probe 460 in three dimensions. Alternatively or in combination, the first angle sensor 495 may comprise a goniometer to determine an angle of treatment probe 450 along an elongate axis 451 of the treatment probe. The second angle sensor 497 may comprise a goniometer to determine an angle of the imaging probe 460 along an elongate axis 461 of the imaging probe 460. The first angle sensor 495 is coupled to a controller 424 of the treatment console 420. The second angle sensor 497 of the imaging probe is coupled to a processor 492 of the imaging console 490. Alternatively or in combination, the second angle sensor 497 may be coupled to the controller 424 of the treatment console 420.

The console 420 comprises a display 425 coupled to a processor system in components that are used to control treatment probe 450. The console 420 comprises a processor 423 having a memory 421. Communication circuitry 422 is coupled to processor 423 and controller 424. Communication circuitry 422 is coupled to the imaging console 490 via the communication circuitry 494 of the imaging console. Arm lock 427 of console 420 may be coupled to the first arm 442 to lock the first arm or to allow the first arm to be freely movable to insert probe 450 into the patient.

Optionally, the console 420 may comprise components of an endoscope 426 that is coupled to anchor 24 of the treatment probe 450. Endoscope 426 can comprise components of console 420 and an endoscope insertable with treatment probe 450 to treat the patient.

In some embodiments, the console 420 comprises impedance sensor circuitry 220 coupled to the energy source to measure impedance of tissue treated with energy from the energy source. In some embodiments, the energy source comprises an electrode and the electrode comprises an impedance sensor. In some embodiments, the processor is configured with instructions to adjust an amount of energy from the energy source in response to an amount of impedance. In some embodiments, the processor is configured with instructions to adjust an amount of deflection of the extension and offset of the energy source from the elongate axis in response to impedance.

In some embodiments, the console 420 comprises force sensor circuitry 210 coupled to a force sensor on the treatment probe. The force sensor can be coupled to the extension to measure tissue resistance related to deflection of the extension, for example. In some embodiments, the force sensor is coupled to the link to measure tissue resistance related to movement of the energy source away from the elongate axis. In some embodiments, the force sensor is coupled to the energy source to measure tissue resistance related to a positioning distance of the energy source from the elongate axis. In some embodiments, the force sensor is configured to measure tissue resistance related to an amount of energy delivery from the energy source.

Optionally, the console 420 may comprise one or more of modules operably coupled with the treatment probe 450 to control an aspect of the treatment with the treatment probe. For example, the console 420 may comprise one or more of an energy source 22 to provide energy to the treatment probe, balloon inflation control 26 to affect inflation of a balloon used to anchor the treatment probe at a target treatment site, infusion/flushing control 28 to control infusion and flushing of the probe, aspiration control 30 to control aspiration by the probe, insufflation control 32 to control insufflation of the target treatment site (e.g., the prostate), or a light source 33 such as a source of infrared, visible light or ultraviolet light to provide optical energy to the treatment probe.

The processor, controller and control electronics and circuitry can include one or more of many suitable components, such as one or more processor, one or more field-programmable gate array (FPGA), and one or more memory storage devices. In some embodiments, the control electronics controls the control panel of the graphic user interface (hereinafter "GUI") to provide for pre-procedure planning according to user specified treatment parameters as well as to provide user control over the surgery procedure.

The treatment probe 450 may comprise an anchor 24. The anchor 24 can anchor the distal end of the probe 450 while energy is delivered to energy delivery region 20 with the probe 450. In some embodiments, the probe comprises a first energy source 250 that can be offset from the elongate axis 451 the probe with an offset 252 a distance to treat tissue, for example with deflection of an extension as described herein. The processor can be configured with instructions to perform 3D volumetric resection of the tissue with rotation, translation and offset of the energy source 250 in response to computer control. The probe 450 may comprise a second energy source as described herein such as a nozzle 200.

The treatment probe 450 may be coupled to the first arm 442 with a linkage 430. The linkage 430 may comprise components to move energy delivery region 20 to a desired target location of the patient, for example, based on images of the patient. The linkage 430 may comprise a first portion 432, a second portion 434 and a third portion 436. The first portion 432 may comprise a substantially fixed anchoring portion. The substantially fixed anchoring portion 432 may be fixed to support 438. Support 438 may comprise a reference frame of linkage 430. Support 438 may comprise a rigid chassis or frame or housing to rigidly and stiffly couple the first arm 442 to treatment probe 450. The first portion 432 can remain substantially fixed, while the second portion 434 and third portion 436 can move to direct energy from the probe 450 to the patient. The first portion 432 may be fixed at a substantially constant distance 437 to the anchor 24. The substantially fixed distance 437 between the anchor 24 and the fixed first portion 432 of the linkage allows the treatment to be accurately placed. The first portion 432 may comprise a linear actuator to accurately position the second energy source such as high-pressure nozzle 200 in the energy delivery region 20 at a desired axial position along an elongate axis 451 of treatment probe 450. Additional actuators and linkages can be provided and operatively coupled to the processor to offset, rotate, and translate the first energy source 250 as described herein.

The elongate axis 451 of treatment probe 450 generally extends between a proximal portion of the probe 450 near linkage 430 to a distal end having anchor 24 attached thereto. The third portion 436 can control a rotation angle 453 around the elongate axis 451. During treatment of the patient, a distance 439 between the energy delivery region 20 and the first portion 432 of the linkage may vary with reference to anchor 24. The distance 439 may adjust with translation 418 of the probe in response to computer control to set a target location along the elongate axis 451 of the treatment probe. In some embodiments, the first portion of the linkage remains fixed, while the second portion 434 adjusts the position of the energy delivery region 20 along the axis 451. The third portion 436 of the linkage adjusts the angle 453 around the axis in response to controller 424 such that the distance along the axis at an angle of the treatment can be controlled very accurately with reference to anchor 24. The probe 450 may comprise a stiff member such as a spine extending between support 438 and anchor 24 such that the distance from linkage 430 to anchor 24 remains substantially constant during the treatment. The treatment probe 450 is coupled to treatment components as described herein to allow treatment with one or more forms of energy such as mechanical energy from a jet, electrical energy from electrodes or optical energy from a light source such as a laser source. The light source may comprise infrared, visible light or ultraviolet light. The energy delivery region 20 can be moved under control of linkage 430 such as to deliver an intended form of energy to a target tissue of the patient.

The imaging console 490 may comprise a memory 493, communication circuitry 494 and processor 492. The processor 492 in corresponding circuitry is coupled to the imaging probe 460. An arm controller 491 is coupled to arm 444 to precisely position imaging probe 460. The imaging console may further comprise a display 425.

In order to facilitate precise control of the treatment probe and/or the imaging probe during treatment of the patient, one or more the treatment probe or the imaging probe may be coupled to a robotic, computer-controllable arm. For example, referring to system 400 shown in FIG. 2, one or both of the first arm 442 coupled to the treatment probe 450 as described herein and the second arm 444 coupled to the imaging probe 460 may comprise robotic, computer-controllable arms. The robotic arms may be operably coupled with one or more computing devices configured to control movement of the robotic arms. For example, the first robotic arm 442 may be operably coupled with the processor 423 of the console 420, or the second robotic arm 444 may be operably coupled with the processor 492 of the imaging console 490 and/or to the processor 423 of the console 420. The one or more computing devices, such as the processors 423 and 492, may comprise computer executable instructions for controlling movement of the one or more robotic arms. The first and second robotic arms may be substantially similar in construction and function, or they may be different to accommodate specific functional requirements for controlling movement of the treatment probe versus the imaging probe.

The robotic arm may comprise 6 or 7 or more joints to allow the arm to move under computer control. Suitable robotic arms are commercially available from several manufacturers such as RoboDK Inc., Kinova Inc. and several other manufacturers.

The one or more computing devices operably coupled to the first and second robotic arms may be configured to automatically control the movement of the treatment probe and/or the imaging probe. For example, the robotic arms may be configured to automatically adjust the position and/or orientation of the treatment probe and/or imaging probe during treatment of the patient, according to one or more pre-programmed parameters. The robotic arms may be configured to automatically move the treatment probe and/or imaging probe along a pre-planned or programmed treatment or scanning profile, which may be stored on a memory of the one or more computing devices. Alternatively or additionally to automatic adjustment of the robotic arms, the one or more computing devices may be configured to control movement of the treatment probe and/or the imaging probe in response to user inputs, for example through a graphical user interface of the treatment apparatus. Alternatively or additionally to automatic adjustment of the robotic arms, the one or more computing devices may be configured to control movement of the treatment probe and/or the imaging probe in response to real-time positioning information, for example in response to anatomy recognized in one or more images captured by the imaging probe or other imaging source (from which allowable ranges of motion of the treatment probe and/or the imaging probe may be established) and/or position information of the treatment probe and/or imaging probe from one or more sensors coupled to the probes and/or robotic arms.

Figures 3A, 3B, 3C:
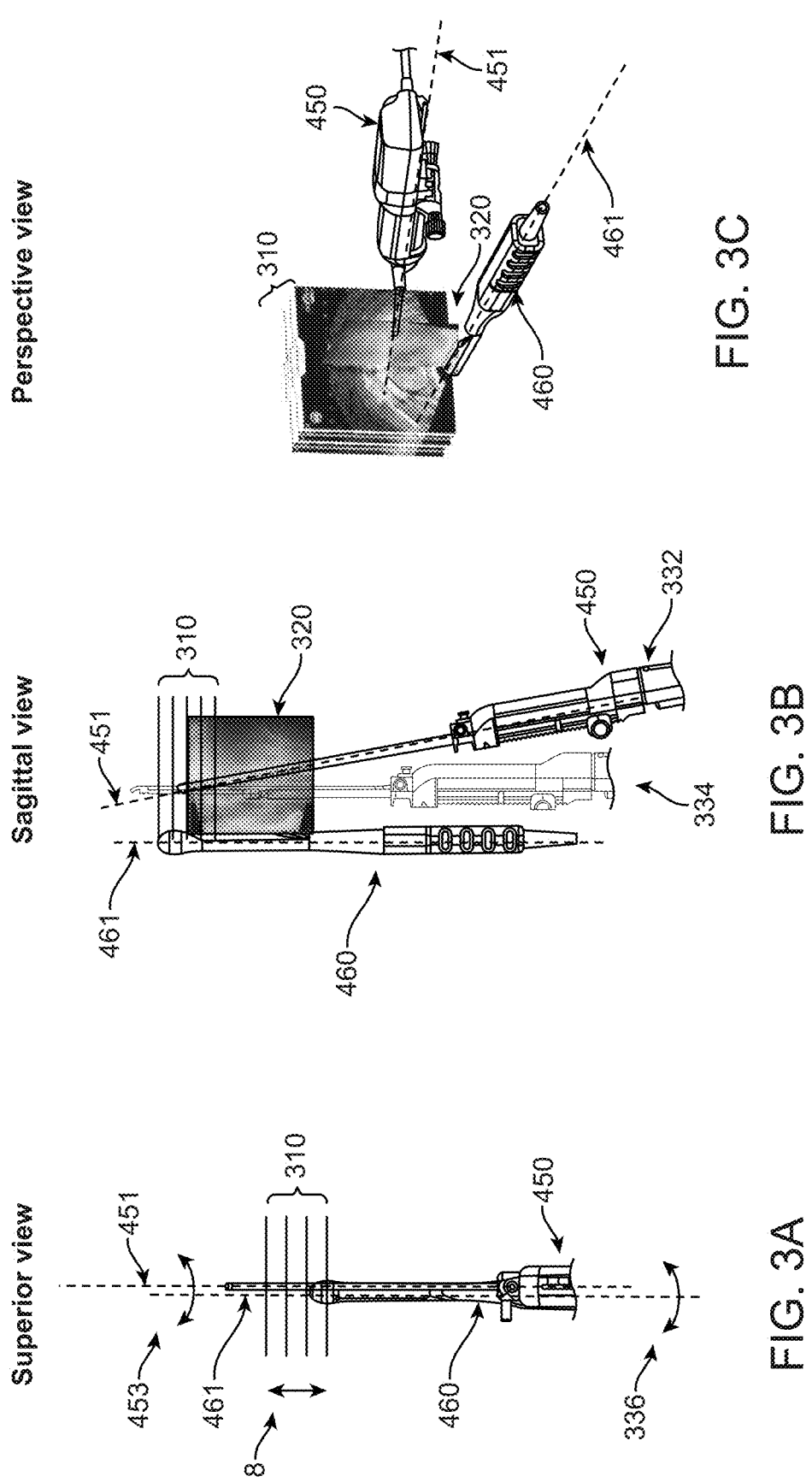
FIG. 3A shows a superior view of an arrangement of probes, in accordance with some embodiments.
FIG. 3B shows a longitudinal view such as a sagittal view of an arrangement of probes, in accordance with some embodiments.
FIG. 3C shows a perspective view of an arrangement of probes, in accordance with some embodiments.

FIGS. 3A, 3B, and 3C show superior, longitudinal (e.g. sagittal), and perspective views, respectively, of an arrangement of probes for use in treatment of tissue. In particular, FIGS. 3A, 3B, and 3C show the relative arrangement, including position and orientation of a treatment probe 450 with respect to the position and orientation of an imaging probe 460 for the treatment of tissue such as prostate tissue. The imaging probe 460 can be configured to generate transverse images such as transverse ultrasound images 310 and one or more longitudinal images such as one or more longitudinal (e.g. sagittal) ultrasound images 320. In some embodiments, the energy source of treatment probe 450 is moved with rotation angle 453 and translation 418, such that the treated tissue and the energy source are within the field of view of the imaging probe 460.

As shown in the superior view of FIG. 3A, the treatment probe axis 451 and the imaging probe axis 461 are positioned in a substantially coplanar configuration, such that the imaging probe and the treatment probe extend along a common plane. As shown in the superior view of FIG. 3B and the perspective view of FIG. 3C, the treatment probe axis 451 and the imaging probe axis 461 are positioned in a substantially coplanar and non-parallel configuration, such that the imaging probe and the treatment probe substantially extend along a common plane, which allows the imaging probe to image the treatment probe along the length of translation 418 with one or more longitudinal images such as real time longitudinal images, for example real time sagittal images. In some embodiments, the treatment probe and the imaging probe are arranged in a substantially coplanar configuration, and the ultrasound probe is rotated to rotate the longitudinal (e.g. sagittal) field of view of the imaging probe in order to image the treatment probe along a length of the longitudinal field of view. Referring again to FIG. 3A, the imaging probe 460 can be rotated about elongate axis 461 by an angle 336 to align the treatment probe 450 so as to be within the sagittal field of view, such that the sagittal field of view of the imaging probe is aligned with elongate axis 451 of the treatment probe, for example.

One or more of the treatment probe or the imaging probe can be moved to adjust alignment between the imaging probe and the treatment probe. In some embodiments, the proximal portion of treatment probe is moved from a first position to a second position. Referring again to FIG. 3B, the treatment probe 450 can be moved from a first position 332 to a second position 334 to adjust alignment between the probes, for example based on data from one or more fiducials as described herein.

In some embodiments, the imaging probe 460 and the treatment probe 450 are aligned to be substantially coplanar with each other within a margin of error so that the imaging probe 460 can image the treatment probe 450 and the treatment probe's energy source during treatment, for example with the treatment probe located within a field of view of the imaging probe such as a longitudinal (e.g. sagittal) image field of view. In some embodiments, the treatment probe is aligned with the imaging probe, such that the treatment probe is visible along a length of a longitudinal (e.g. sagittal) view of the imaging probe.

In some embodiments, the imaging probe 460 and the treatment probe 450 may be somewhat misaligned, e.g. by more than the margin of error, such that the treatment probe may disappear from a portion of the longitudinal (e.g. sagittal) image because part of the imaging probe extends beyond the longitudinal (e.g. sagittal) field of view, for example. In some embodiments, this may result in the imaging probe 460 not imaging a portion of the treatment with the longitudinal (e.g. sagittal) images. In some embodiments, the treatment probe 450 and the imaging probe 460 may be arranged in a substantially skewed orientation as described herein, e.g. outside the margin of error, such that the treatment probe extends outside the longitudinal (e.g. sagittal) field of view of the imaging probe but is located within the field of view of transverse images of the imaging probe. In such embodiments, the treatment can be monitored in real time with transverse images, in which the imaging probe moves to maintain the energy source and concurrently treated tissue within the transverse field of view of the imaging probe. In some embodiments, a transverse view of the tissue and energy source can decrease sensitivity to alignment between the two probes, and the imaging probe can be moved with the energy source, for example synchronously, to image the tissue and the energy source during treatment.

Figure 4:
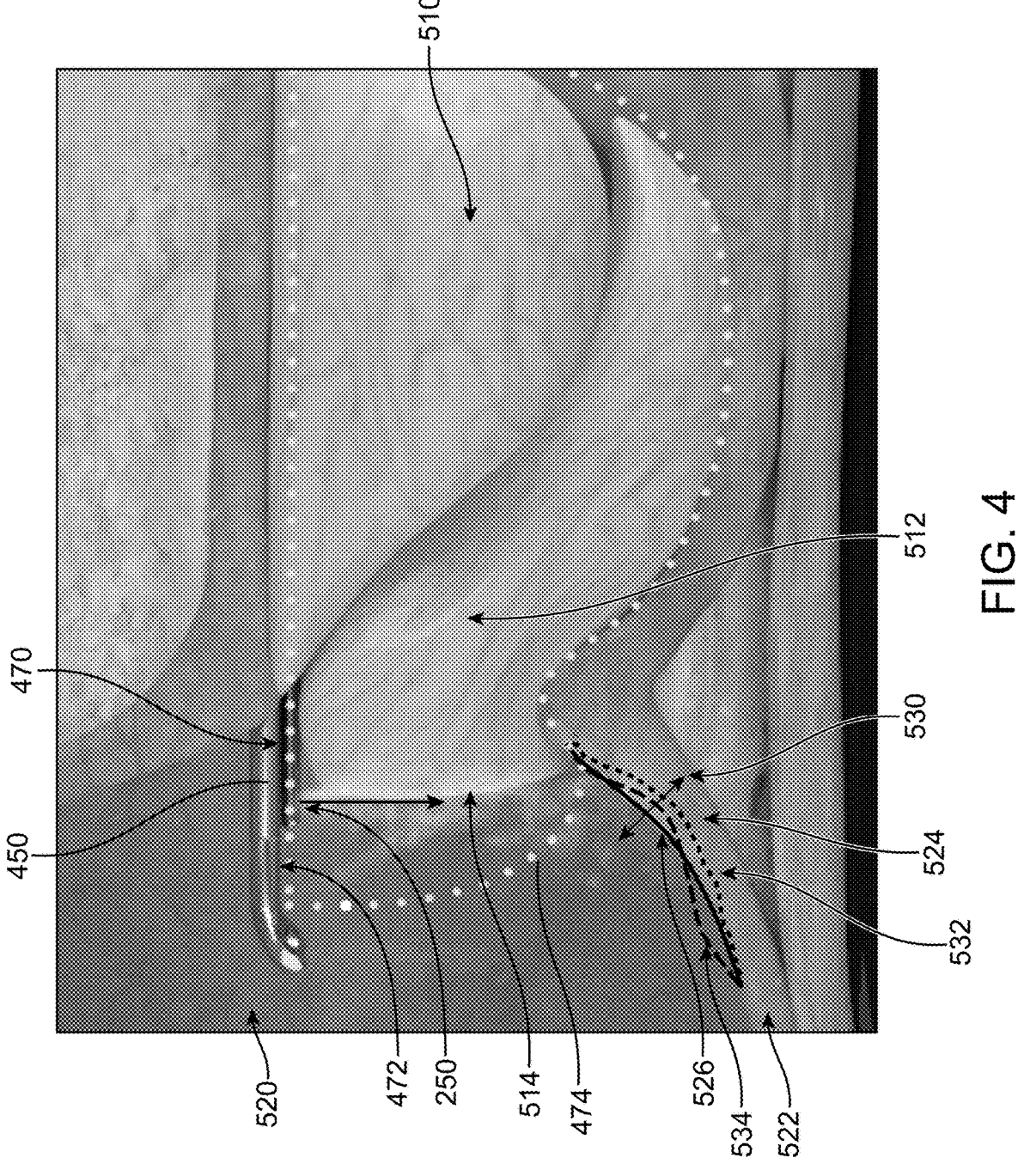
FIG. 4 shows a treatment of a patient, in accordance with some embodiments.

FIG. 4 shows a treatment of a tissue a patient. The treatment probe 450 may be inserted into a lumen of the patient, such as along urethra of the patient, to treat a distal portion of the treatment area with an energy source. In some embodiments, treatment probe 450 comprises an evacuation port 472, which may be coupled to a source of aspiration as described herein. In some embodiments, the treatment probe 450 is configured to release energy from an energy source 250, and the treatment probe may comprise an energy treatment probe 470 configured to release energy from the energy source 250 with rotation and translation as described herein. In some embodiments, the energy source of the treatment probe 470 is configured to rotate and translate with respect to other components of treatment probe 451, such as the aspiration ports. A treatment profile 474 is shown by a dotted line. As shown, the resection procedure has begun and the energy treatment probe 470 has been moved proximally from a distal end of the treatment profile 474, such that tissue has been removed from the distal portion of the distal treatment area in accordance with treatment profile 474. In some embodiments, the aspiration port actively aspirates fluid and tissue products during the procedure and may comprise a component of a fluid management system. In some embodiments the energy source of the energy treatment probe is rotated through an angle and translated along a length specified of the treatment profile in accordance with a treatment profile shown on a user interface. In some embodiments, the depth of resection is controlled in accordance with a treatment profile based upon the user input into the user interface.

The first tissue treated with the energy source may comprise any suitable tissue as described herein, such as a tissue first organ, and the second tissue that is imaged with the first tissue may comprise any suitable tissue as described herein, such as a tissue of a second organ. The first tissue may comprise a tissue of a prostate 510, and the second tissue may comprise a tissue of a bladder 520, for example. In some embodiments, the prostate 510 comprises a medial lobe 512, in which a distal portion of the medial lobe 512 extends into the bladder 520 so as to comprise and intravesical prostatic protrusion 514. In some embodiments, the bladder 520 comprises a wall 522 and a trigone tissue 524. In some embodiments, the trigone tissue comprises tissue of a region of bladder tissue generally defined by the entrance of the ureters to the bladder at the two ureteric orifices and the opening of the urethra into the bladder at the internal urethral orifice. In some embodiments, the second tissue comprises a wall of tissue such as bladder wall 522. The edge of the second tissue may comprise a profile 526, which can be monitored, for example imaged, in real time while the first tissue is treated to assess the effect of the energy source on the second tissue, e.g. the trigone, from the treatment of the first tissue, e.g. the prostate.

While the imaging device used to generate the images may comprise any suitable imaging device as described herein, in some embodiments the imaging device comprises a real time ultrasound imaging device such as a probe with a frame rate within a range from about 5 Hertz (Hz) to about 250 Hz and a latency from when an imaging energy is released from the imaging device until an image is shown on the display within a range from about 10 milliseconds (ms) to about 1000 ms.

While the second tissue can be monitored in many ways, in some embodiments the second tissue comprises a structure with sufficient contrast in an image to identify the structure of the second tissue. In some embodiments, the tissue structure comprises a wall of tissue, such as a wall of an organ such as the bladder. Data from the image of the tissue structure can be processed to determine information from the tissue structure, such as one or more of a shape profile, a contrast, a slope, a movement or a blur of the tissue structure. In some embodiments, the tissue structure comprises a surface profile 526 of a second tissue that moves with a movement 530 in response to the energy source treating the first tissue. In some embodiments, the surface profile 526 moves from a first profile to a second profile 532 and a third profile 534, which can be sequentially viewed in real time images of the second tissue. The movement of the second tissue in response to the treatment of the first tissue may comprise one or more of stretching, compression, rotation, translation, deflection, or deformation, for example. In some embodiments, the processor is configured to detect movement of the second tissue in response to treatment of the first tissue and adjust the energy source.

When used in the illustrated example of FIG. 4 and elsewhere herein, the terms "proximal" and "distal" are from the perspective of the surgical system. Thus, the distal end of the treatment probe is the portion of the probe inserted farthest into the patient.

Figure 5:
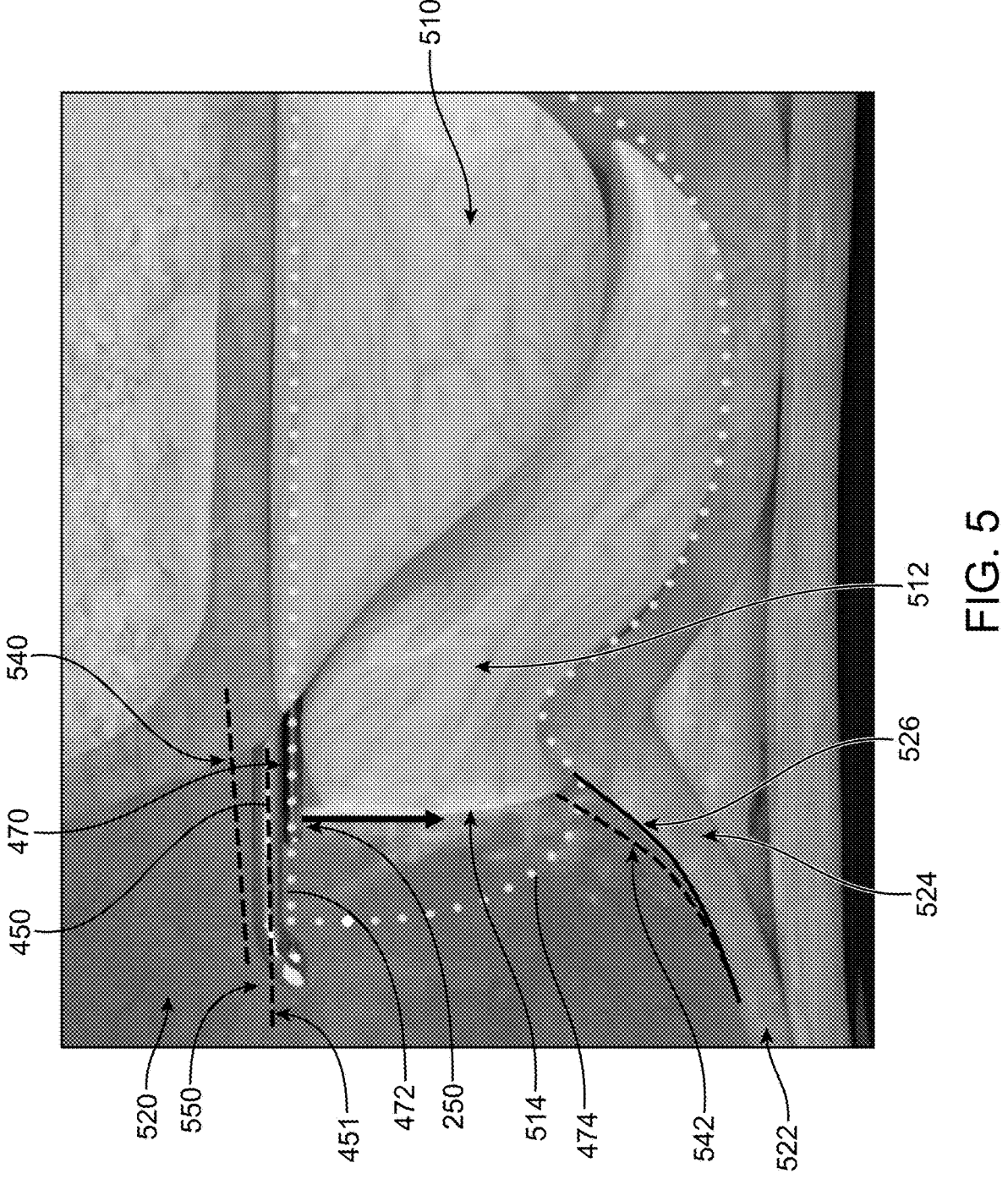
FIG. 5 shows a probe placed in a first tissue and a response of a second tissue to the probe placed in the first tissue, in accordance with some embodiments.

FIG. 5 shows a probe 450 placed in a first tissue, such as the prostate 510, and a response of a second tissue, such as bladder wall 522, to the probe placed in the first tissue. The probe 450 and elongate axis 451 of the probe are shown placed at an adjusted position 550 to decrease the response of the second tissue to placement of the probe 450 in the first tissue. In some embodiments, the engagement of the probe with the first tissue such as the prostate 510 can result in tension or compression of the second tissue such as the bladder wall 522 that moves the second tissue away from its natural position and orientation with respect to other tissues. An initial position and orientation of the elongate axis of the probe is shown with a dashed line 540. At the initial position and orientation of the probe placed in the first tissue, e.g. the prostate, the position of the second tissue such as tissue of the bladder wall 522, can be altered in response to placement of the probe as shown with dashed line 542. In some embodiments, the placement of the probe in the first tissue results in tenting of the second tissue, such that the surface profile of the second tissue appears elevated in one or more images of the second tissue such as series of real time images of the second tissue. Alternatively, the second tissue may appear compressed in the one or more images. The one or more images may comprise any suitable images as described herein, such as one or more longitudinal (e.g. sagittal) images 320, or one more transverse images 310, and combinations thereof, for example. In some embodiments, the one or more images comprise a plurality transverse images, such as a series of transverse images to detect lateral stretching of the tissue from a first side of the probe toward a second side of the probe.

The processor as described herein can be configured to process the image data to generate an output to move the probe in response to one or more of an image of the probe or force sensor data related to tissue engagement of the probe as described herein. In some embodiments, the output is provided with a user interface such as a display to provide an indication to a user to adjust the position of the probe. Alternatively or in combination, the output may comprise instructions to a robotic arm to adjust the position of the probe. In some embodiments, the output instructions to move the robotic arm are combined with a first user input to confirm the movement of the probe prior to moving the probe with the robotic arm and to confirm that the repositioned probe is suitable based on a second user input. Although reference is made to a robotic arm, the probe can be adjusted manually, for example with user manipulation of the proximal end of the probe.

Figure 6:
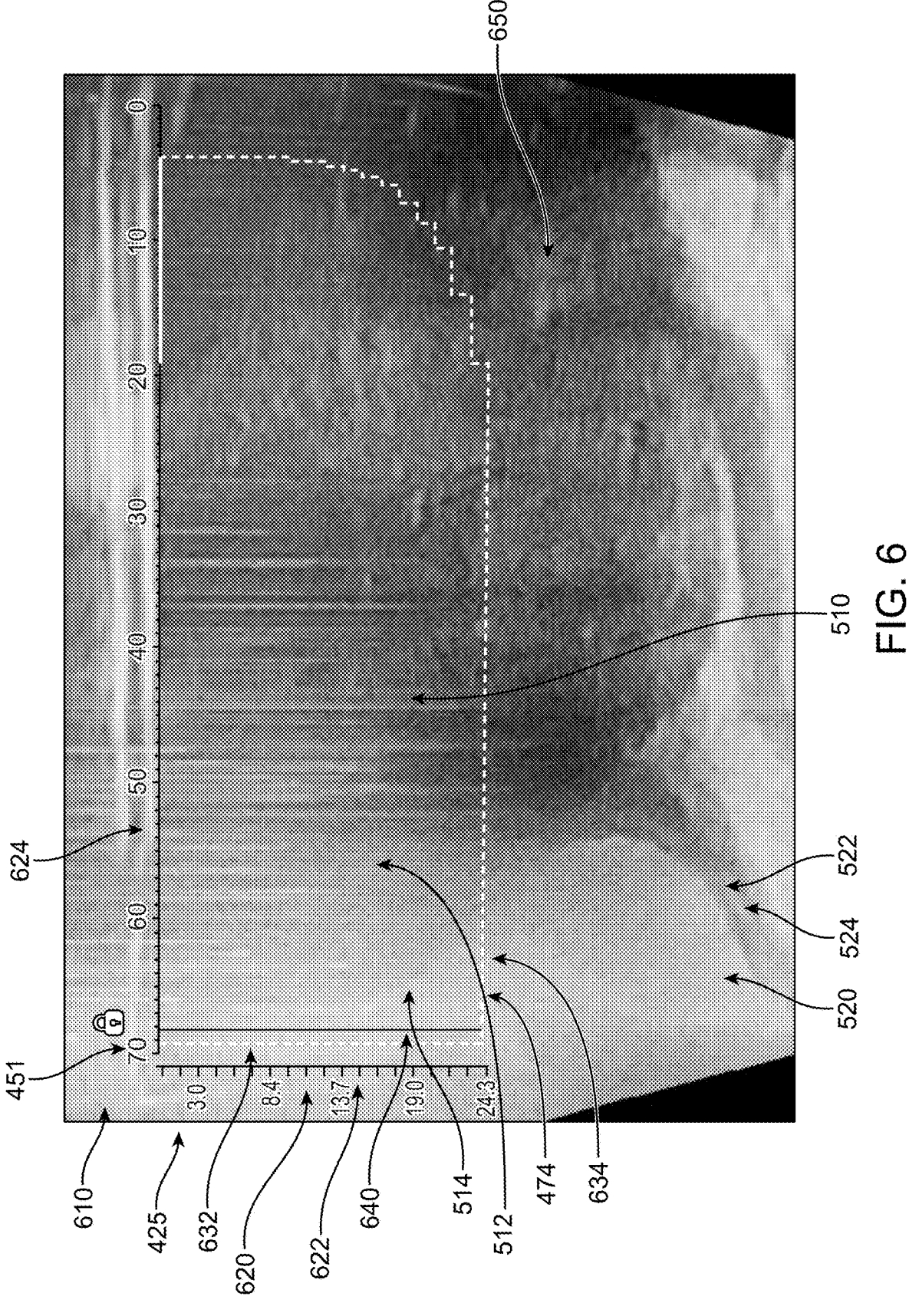
FIG. 6 shows an image of a treatment probe with identifiable tissue structures that can be processed to determine the position and location of tissue structures, in accordance with some embodiments.

FIG. 6 shows an image 610 of a treatment probe 451 with identifiable tissue structures that can be processed to determine the position, location, size, shape and contour of tissue structures as described herein. The image 610 can be shown on a display 425 as described herein. The identifiable tissue structures shown in the image on the display may comprise any suitable tissue structure as described herein. In some embodiments, the one or more tissue structures comprises one or more of the prostate 510, the medial lobe 512, the intravesical prostatic protrusion 514, the bladder 520, the bladder wall 522, the edge of the bladder wall between the wall 522 and the interior of the bladder 520, the trigone tissue 524, or a verumontanum 650 of the prostate 510, for example. One or more of the identified tissue structures can be shown on the display. In some embodiments, an initial profile of the one or more identified structures is highlighted on the display at a first time, for example with a first modification to pixels of first image, and as the treatment progresses, the one or more structures can be shown on the display at a second time with a second modification to pixels of a second image, which can allow the user to visualize the progress of the treatment and make adjustments when helpful.

The image 610 may comprise one or more images of the tissue shown on the display, such as real time images of the tissue and the probe. The one or more images can be generated with any suitable imaging apparatus as described herein, such as a transrectal ultrasound probe, for example. The one or more images may comprise one or more of a longitudinal image, a sagittal image or a transverse image, for example. The treatment profile 474 can be overlaid on the one or more images, and the treatment profile may comprise a three dimensional treatment profile, for example. In some embodiments, a reticle 620 is overlaid on the image of the tissue to show the relative scale of the tissue shown on the display in relation to the tissue and the treatment profile 474. The reticle 620 may comprise a radially extending component 622 that extends away from the elongate axis of the treatment probe 450 and a longitudinally extending component 624 that extends along the elongate axis of the treatment probe 450. The treatment profile 472 may comprise a radial component 632 that corresponds to a distance away from the energy source and the elongate axis of the probe a longitudinal component 634 that corresponds to a distance along the elongate axis of the probe, which may correspond to the position of the energy source along the elongate axis during treatment. In some embodiments, the processor is configured with instructions to overlay a treatment marker 640 on the image of the tissue, in which the marker corresponds to the longitudinal position of the energy source along the treatment axis.

While the treatment profile can be generated in many ways, in some embodiments, the treatment profile comprises a three dimensional (3D) treatment profile generated from a plurality of images, such as a treatment profile generated from a longitudinal image such as a sagittal image and a plurality of transverse images. In some embodiments, the 3D treatment profile comprises a 3D volumetric tissue removal profile. Examples of user interfaces for generating three dimensional treatment profiles from transverse and longitudinal (e.g. sagittal) images are described in PCT/US2019/038574, filed Jun. 21, 2019, entitled "ARTIFICIAL INTELLIGENCE FOR ROBOTIC SURGERY", published as WO2019246580A1 on Dec. 26, 2019, the entire disclosure of which has been previously incorporated herein by reference.

Figure 7:
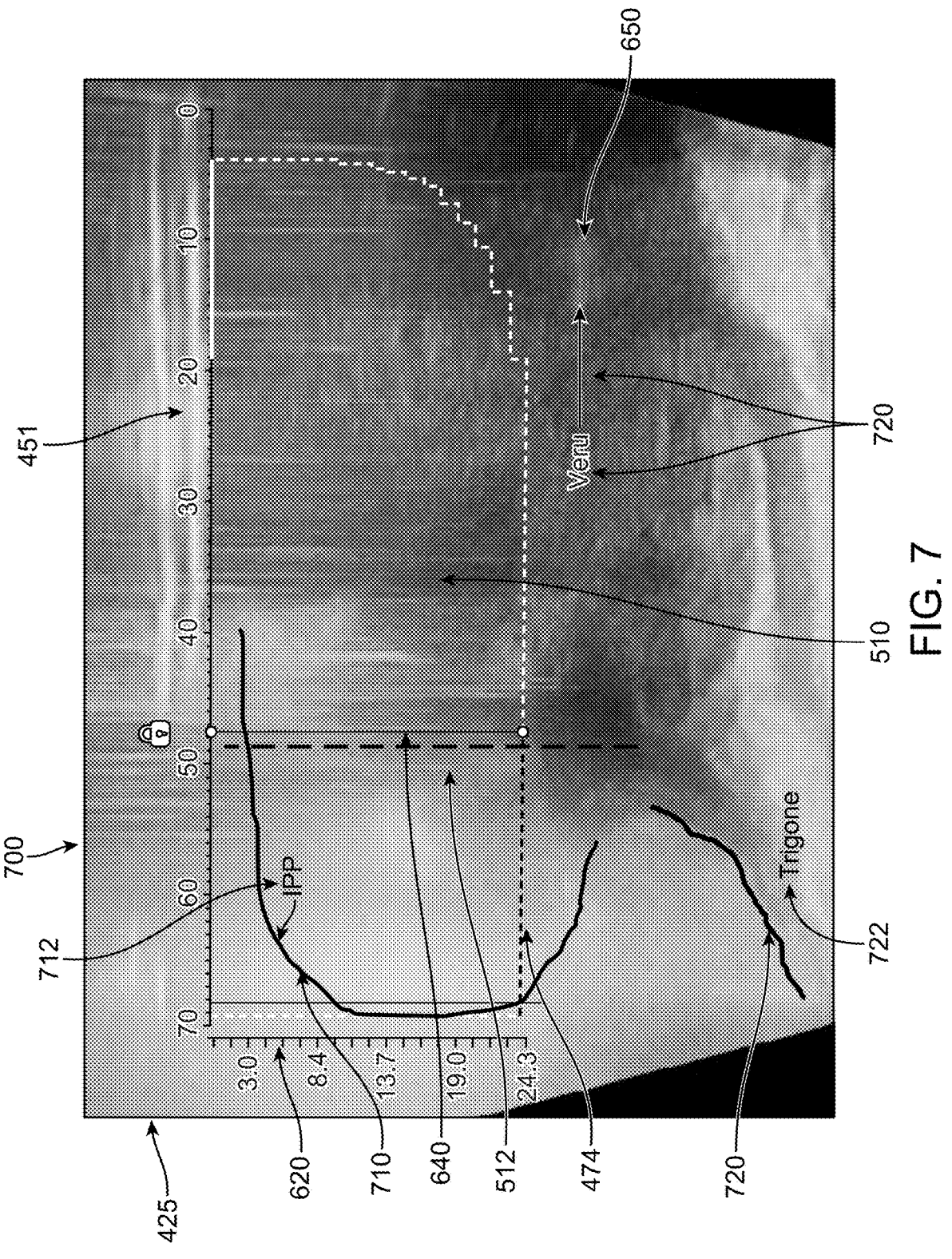
FIG. 7 shows identified tissue structures on an image of a patient shown on a display during treatment, in accordance with some embodiments.

FIG. 7 shows identified tissue structures of an image 700 from a patient shown on a display 425 during treatment. The identified tissue structures shown on the image can be emphasized for the user to see, for example with highlighting or other pixel modification of the image such as markers. In some embodiments, the first tissue such as prostate 510 highlighted. Alternatively or in combination, a boundary

720 of the second tissue such as the trigone is highlighted and may be identified with markers such as one or more labels 722.

In some embodiments, an initial profile of the one or more of the first tissue or the second tissue is shown on the display 425 and overlaid on subsequent images. For example an initial profile 710 of the intravesical prostatic protrusion ("IPP") can be shown on the display and overlaid on subsequent images and can be identified with markers such as one or more labels 712. This can allow the user to compare the real time image of the tissue with the initial profile. For example, the treatment marker 740, the image 700 and the initial profile 710 can be used to evaluate the progress of the treatment. Alternatively or in combination, the initial profile of the second tissue can be shown on the display and overlaid on subsequent images to evaluate the effect of the treatment on the second tissue.

Figure 8:
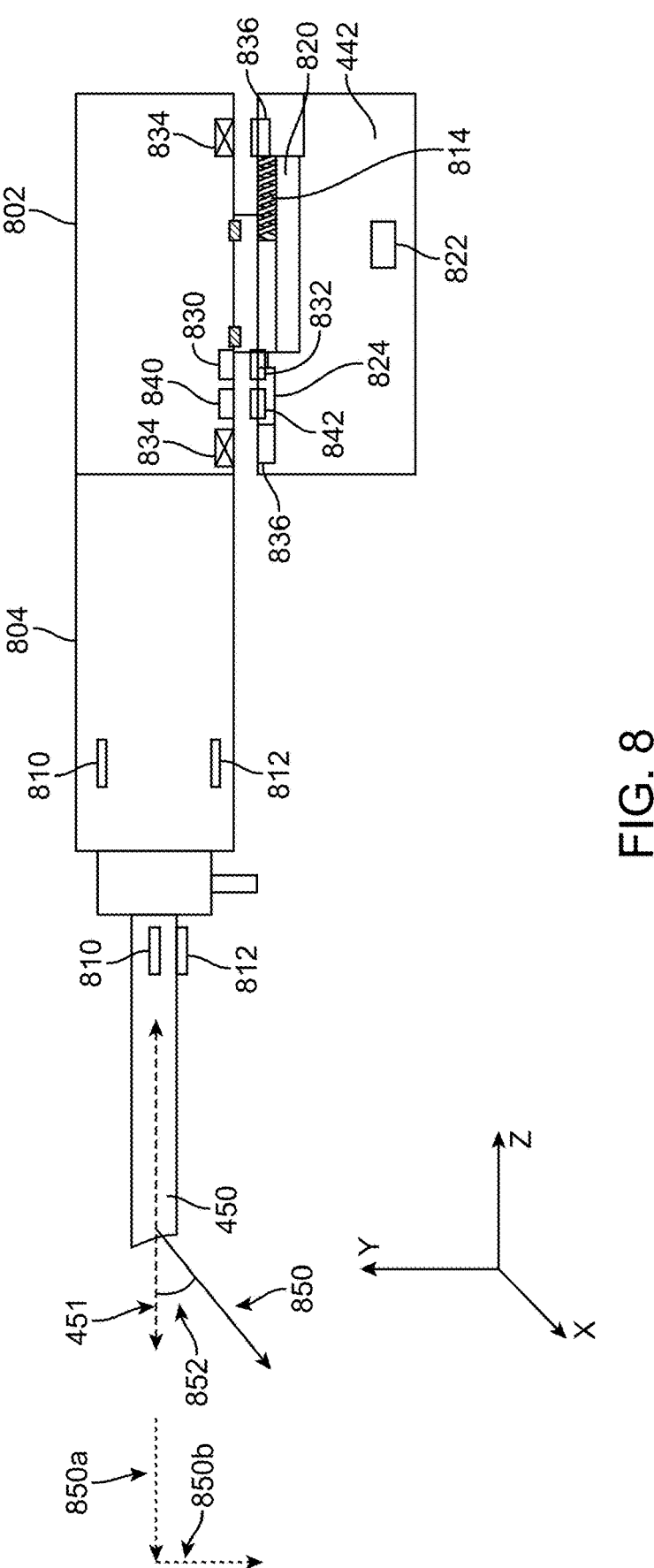
FIG. 8 shows an arm coupled to a probe with sensors configured to measure tissue pulling on the probe in response to placement of the probe, in accordance with some embodiments.

FIG. 8 shows the arm 442 coupled to a probe with sensors configured to measure a force 850 from tissue pulling on the probe 450 in response to placement of the probe. In some embodiments the force 850 comprise a first component 850*a* and a second force component 850*b*, which is measured by the one or more sensors to determine an orientation and a magnitude of the forces exerted on the distal portion of the probe by the tissue. In some embodiments, the second force component 850*b* corresponds to stretching of tissue, such as stretching of a second tissue in response to placement of the probe in a first tissue as described herein. In some embodiments, the first component 850*a* corresponds to the tissue pulling the probe distally, e.g. away from the handpiece 804, along a direction corresponding to elongate axis 451 of the probe. Alternatively or in combination, the first component 850*a* may correspond to the probe pressing tissue, for example with tissue pressing into the probe along elongate axis 451. Work in relation to the present disclosure suggests that a natural lumen such as the urethra engaging a probe can provide at least some frictional resistance to movement of the probe. The amount of force pulling on the probe can be within a range from about 0 Newtons ("N") to about 12.2 N. In some embodiments, the first force component 850*a* comprises a longitudinal force component and the second force component 850*b* comprises a radial force component. In some embodiments, the first force component is within a range from about 0 N to about 2 N, and the second force component is within a range from about 0 N to about 12 N.

In some embodiments, the processor is configured to provide an indication to a user to adjust the probe in response to the amount of force to the probe, for example a force greater than about 12 N. In some embodiments, the processor is configured to generate the notification if a combined force component is greater than about 6 N, for example. Alternatively or in combination, the processor can be configured to generate the notification if either force component is greater than about 5 N, for example. In some embodiments, the processor is configured to provide the indication if the force on the probe along the longitudinal axis of the probe is greater than a first amount or if the radial component is greater than a second amount. For example, the processor can be configured to generate the first notification if the first force component is greater than about 1 N or if the second force component is greater than about 5 N. In some embodiments, the indication comprises a first indication if the longitudinal component is greater than the first amount and a second indication if the radial component is greater than the second amount. For example, the processor can be configured to generate the first indication if the amount of force in the longitudinal direction is greater than about 2 N and generate the second notification if the radial force is greater than about 12 N or generate the first notification if the longitudinal force is greater than about 1N and generate the second notification if the radial force is greater than about 5N. These values are exemplary, and any suitable values can be used as will be understood by one of ordinary skill in the art.

In some embodiments, the radial component corresponds to an amount of force along a plane transverse to the elongate axis of the probe, for example perpendicular to the elongate axis of the probe. In some embodiments, the radial component comprises a combination of force vectors along the plane transverse to the elongate axis of the probe. For example, the force vectors may comprise components of a three dimensional (3D) force vector, in which the first force component corresponds to a 3D force vector component along the axis of the probe and the second force component comprises a radial component corresponding to second and third 3D force vector components that are perpendicular to the first 3D force vector component.

While the force 850 can be measured in many ways, in some embodiments the force 850 is measured with the probe in a substantially fixed first position. In some embodiments, the probe is moved to a second position to reduce the force to the probe from the tissue. The second position may comprise a substantially fixed position to measure the force to the probe at the second position. The force 850 measured at the first position and the second position may comprise one or more force components at each position such as first component 850*a* and second component 850*b*.

In some embodiments, image data is combined with the force sensor data to determine whether the probe placement is suitable to decrease tissue stretching as described herein. The image data may comprise any suitable image data as described herein, such as image data from one or more of the first tissue or the second tissue. In some embodiments, the image data comprises image data from the first tissue. Alternatively or in combination, the image data may comprise image data from a second tissue such as the bladder wall as described herein. In some embodiments, first image data of the tissue acquired prior to placement of the probe is compared to second image data acquired after the probe has been placed, and the data from the comparison is combined with the force sensor data to determine whether to adjust the probe.

While the one or more sensors can be calibrated in many ways, in some embodiments the one or more sensors are calibrated to measure tissue forces pulling on the probe. Alternatively or in combination, the sensors can be calibrated to measure compressive forces from tissue pushing on the probe as described herein. In some embodiments, the force sensor data from the one or more sensors is calibrated to provide a zero force reading when the probe has been placed on the arm in a free standing configuration. The calibration data may comprise offset values for the one or more sensor readings corresponding to the free standing configuration. The calibration data may be stored on one or more components of the processor as described herein. The calibration data may comprise one or more parameters to convert the sensor readings to force values corresponding to the amount of force on the probe, such as the amount of force from the first component and the amount of force from the second component.

In some embodiments, one or both of the arms coupled to the treatment probe and the imaging probe may comprise one or more sensors to detect tissue forces on the one or more probes in response to placement of the one or more probes in the tissue. In some embodiments, tissue pulling on the probe in response to placement of the probe is measured with the one or more sensors located on one or more of the probe, the handpiece, handpiece, or the instrument driver such as a motor pack as described herein. In some embodiments, tissue engaging the distal portion of the probe responds to the placement of the probe with at least one force 850 that corresponds to stretching of the tissue. The at least one force 850 may comprise one or more components, such as a force component pulling the probe distally away from the hand piece or a radial force component, and combinations thereof, for example.

Referring again to FIGS. 1 and 2 one or more of the first 442 or the second arm 444 may be operably coupled with a force sensor configured to detect tissue pulling on the one or more probes in response to placement of the probe. In some embodiments, the arm 442 is coupled to a motor pack 802. The arm 442 may comprise any suitable arm as described herein, such as a robotic arm or a manually positionable arm, for example. The motor pack 802 may be coupled to a hand piece 804 of the probe 450 to move the probe with one or more linages as described herein.

Examples of robotic arms and linkages suitable for use in accordance with the present disclosure are described in PCT/US2020/021756, filed Mar. 9, 2020, entitled "ROBOTIC ARMS AND METHODS FOR TISSUE RESECTION AND IMAGING", published as WO/2020/181290, and PCT/US2019/038574, filed Jun. 21, 2019, entitled "ARTIFICIAL INTELLIGENCE FOR ROBOTIC SURGERY", published as WO2019246580A1 on Dec. 26, 2019, the entire disclosure of which have been previously incorporated herein by reference.

According to some embodiments, one or more X-direction force sensors 810, one or more Y-direction force sensors 812, and/or one or more Z-direction force sensors 814 may be provided on the robotic arm 442, the hand piece 804, and/or the probe 450.

In some embodiments, the handpiece 804 and treatment probe 450 are sterile and configured for single use, and the motor pack 802 and arm 442 comprise non-sterile reusable components. The handpiece 804 may comprises linkages to move the energy source, for example with rotation and translation as described herein. The sensors to measure the force to the probe 450 may comprises one or more sensors located on the motor pack 802 where it connects to the arm 804, for example. In some embodiments, the one or more X-direction force sensors 810, the one or more Y-direction force sensors 812 and the one or more Z-direction force sensors 814 are located where the motor pack 802 connects to arm 442. In some embodiments, the sensors comprise one or more load cells. The sensors may comprise calibrated sensors to measure the force of tissue to the probe 450. While the sensors can be configured in many ways, in some embodiments the one or more X-direction force sensors 810 and the one or more Y-direction force sensors 812 are configured to measure radial forces in response to tissue pulling on the arm, which may comprise a moment, and the Z-direction force sensor is configured to measure forces along the axis 451 of the probe 450, for example.

The one or more force sensors may comprise a strain gauge, a pressure sensor, or a piezo electric transducer, for example. In some embodiments the strain gauge comprises any of a number of configurations of a Wheatstone bridge. A Wheatstone bridge circuit converts a small change in resistance into a measurable voltage differential, which can be equated to an applied force. The force sensor may be coupled to the handpiece, such as any hand piece embodiment described herein. In some instances, one or more force sensors are operatively coupled to the imaging probe, treatment probe, or both.

In some embodiments, the circuitry for operating the force sensor is insulated and isolated from the imaging probe and treatment probe. This allows the probe to satisfy any patient leakage current requirements and reduces any noise that would be picked up by the probe, thus enhancing the signal to noise (S/N) of the force sensor. In some embodiments, the signal wires from the force sensor may be twisted together and optionally may be shielded to maintain signal integrity, improve immunity, and maintain an adequate S/N ratio. The force sensor may be formed of any suitable material, and in some cases, is formed of a biocompatible material for portions of the sensor that may come into contact with a patient before, during, or after treatment.

In some embodiments, one or more force sensors are sized to fit on or within the probe shaft, such as the imaging probe or treatment probe shaft. The force sensor may be configured with any suitable strain sensitivity "k," which is a proportional factor between the relative change of the resistance. The strain sensitivity is a figure that is dimensionless and is called the Gage Factor ("GF"). A linear pattern strain gauge may be used to measure strain in a single direction on the handpiece. Conductive signal wires may be bonded to the pads of the sensor which carry the signal to an input amplifier. One or more sensors may be bonded to one or more probes on a carrier substrate that may insulate the sensor from any metal of the probe, such as a metal probe shaft.

Displacement in the Z-direction of the handpiece can be detected by a spring and sensor 814. Utilizing this configuration, the entire probe assembly can be able to slide a suitable distance to provide protection from a probe being driven into a tissue wall. The probe assembly may be arranged on a sliding trolley 820 which can be sprung against a simple spring to provide a constant and known force "K" spring constant. Accurate distance measurement of the handpiece, such as my displacement of the trolley, is possible over a short distance with a suitable arrangement such as less than 2 inches. Other positional encoder linear sensors may be used in combination, or in the alternative. For example, a linear variable differential transformer (LVDT), is an electromechanical sensor used to convert mechanical motion into a variable electrical current and can be used to measure resistance to the insertion force of the probe. An optical encoder, or any of a number of suitable inductive linear encoders. A sensor can measure a force based upon an inductive linear encoder 824 and may be arranged for non-contact to ensure high reliability. A high-resolution encoder 824 may be provided for a linear resolution of between about 15 micrometers for a digital encoder, to about 54 micrometers, such as for an analogue encoder.

One or more sensors may be provided on one or more robotic arms to measure position, orientation, force, or some other parameter. In some instances, two sensors may be part of the robotic arm assembly and can be utilized to determine unintended movements. These sensors can be internal encoders which may be located one or more joints of the robotic arm and may be an inertial measurement unit (IMU) 822. An IMU is an electronic sensor device that measures and reports one or more parameters, such as a force, an angular rate, and/or the orientation of the sensor, and may use a combination of accelerometers, gyroscopes, and/or magnetometers. Some IMUs that are suitable for incorporation into one or more robotic arms may have a full-scale acceleration ranges of ±2/±4/±8/±16 g ("g" values in relation to acceleration due to gravity) and a wide angular rate ranges of ±125/±250/±500/±1000/±2000/±4000 degrees per second ("dps"). The IMUs can detect forces on the robotic arm and communicate the magnitude and/or direction of an external force to the computing devices, such as a robotic control system. The one or more IMUs 822 can provide feedback which can be used to control the one or more robotic arms to compensate for vibration, positional awareness, and stabilization compensation.

As described herein, the arm 442 can be docked with the probe 450 by the use of sensors to aid in one or more of coarse positional alignment, intermediate positional alignment and fine positional alignment. For example, the probe may be associated with a beacon 830, such as an IR beacon, and the robotic arm 442 may carry an IR receiver 832 that is able to detect an emission from the IR beacon 830 for coarse alignment. One or more alignment fiducials 834 may be associated with the probe 450 and one or more alignment sensors 836 may be associated with the robotic arm 442. The alignment sensors 836 are able to detect the position of the alignment fiducials, and thus determine the position of the robotic arm 442 relative to the probe 450, as described herein. In some embodiments, proximity sensors such as Hall effect sensors or proximity switches are used to detect the alignment between the probe and the arm in order to engage the probe with the arm, for example to latch the probe onto the arm when the arm has been suitably manipulated into position.

In some embodiments, when the treatment has been completed, the arm can be decoupled from the probe while the user holds the probe, and the arm drawn away from the probe, for example automatically drawn away from the probe.

In some embodiments, the first arm 442 and the second arm 444 comprise robotic arms, for example as shown with reference to FIGS. 1 and 2. The one or more computing devices operably coupled with the robotic arms (such as the processor of the console 420 or console 490 as described herein) may comprise instructions to control movement of the robotic arms in response to forces detected by the sensor, for example to prevent over-compression or stretching on of the anterior tissue and resultant damage to the tissue and/or the probe. In the exemplary use case of the treatment system for prostatic tissue resection, the treatment probe is ideally positioned at the anterior center of the prostate cavity of the patient, but without over compressing the anterior prostate to prevent inadvertent injury to the urethra/prostate (e.g., excessive bleeding, necrosis, perforation of tissue) and/or damage to one or both of the imaging probe and the treatment probe. Similarly, the imaging probe, which can be a TRUS probe, is ideally positioned within the rectum of the patient with adequate anterior compression to view the prostate and the treatment probe, but without over compressing the tissue, so as to avoid inadvertent injury to the rectum (e.g., bleeding or perforation of the tissue) and/or damage to one or both of the imaging probe and the treatment probe. The treatment probe, the first robotic arm coupled thereto, the imaging probe, and/or the second robotic arm 444 coupled thereto may be provided with the force sensor configured to detect anterior compression or stretching of the tissue with the probe. The detected force level may be communicated to the processor operably coupled with the robotic arm and compared to a threshold value of force pre-programmed or stored in the memory of the computing system. If the detected force exceeds the threshold, the movement of the robotic arm may be adjusted to move the probe away from the anterior tissue, thereby at least partially relieving compression or stretching of the anterior tissue.

Figure 9A:
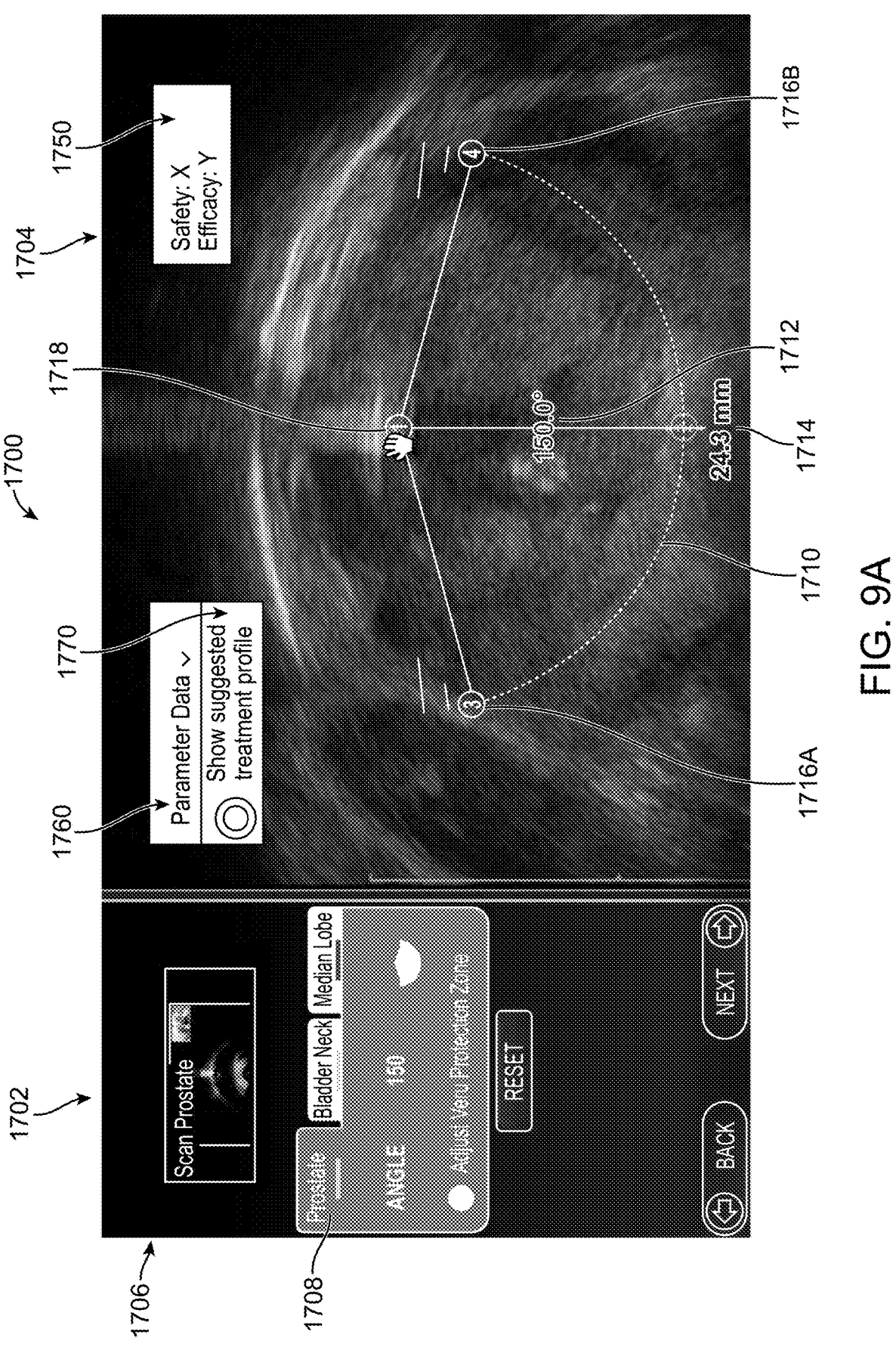
FIGS. 9A to 9C show a user interface screen of a system with one or more transverse images of a tissue and a treatment profile.
Figure 9B:
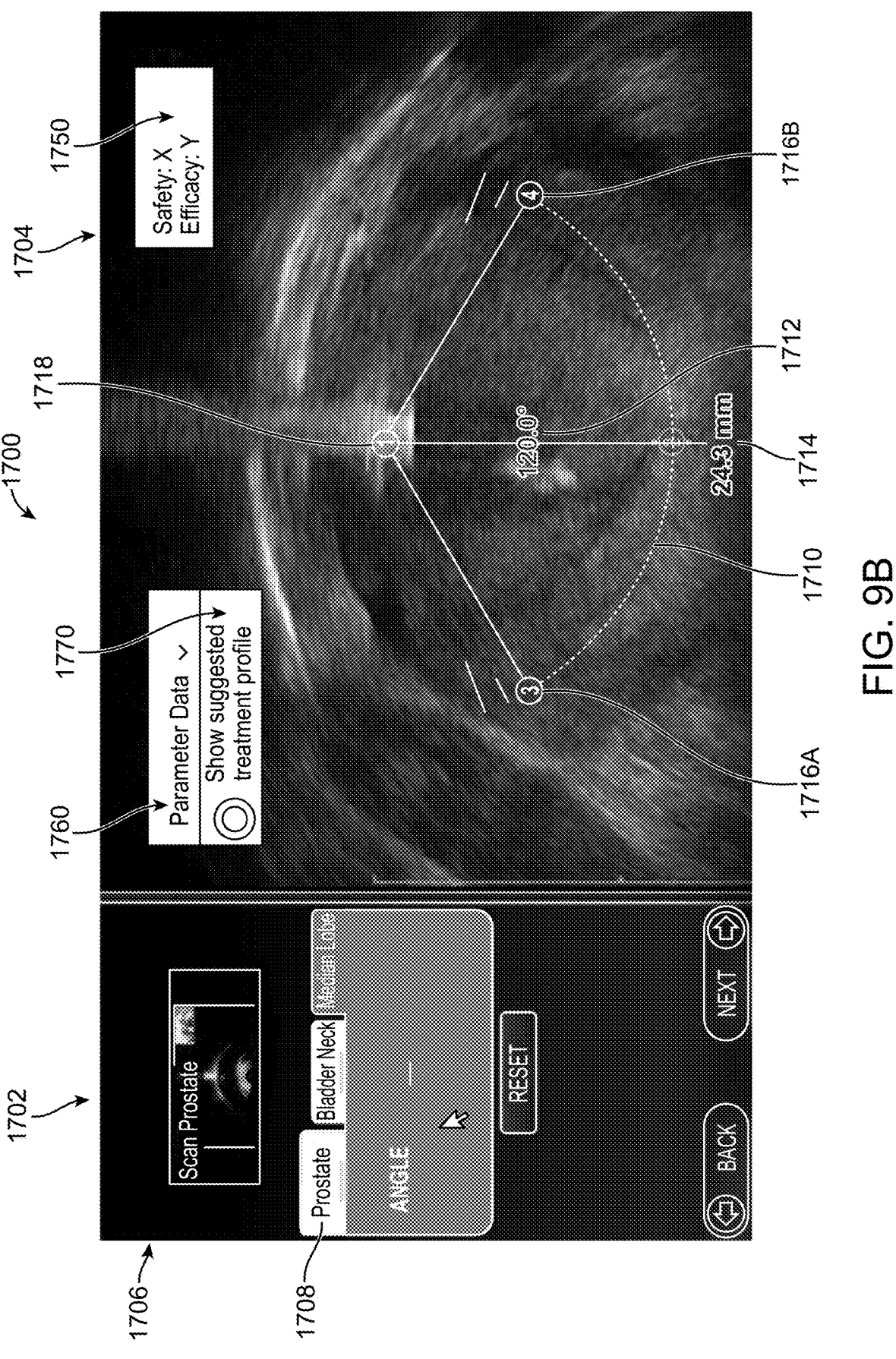
Figure 9C:
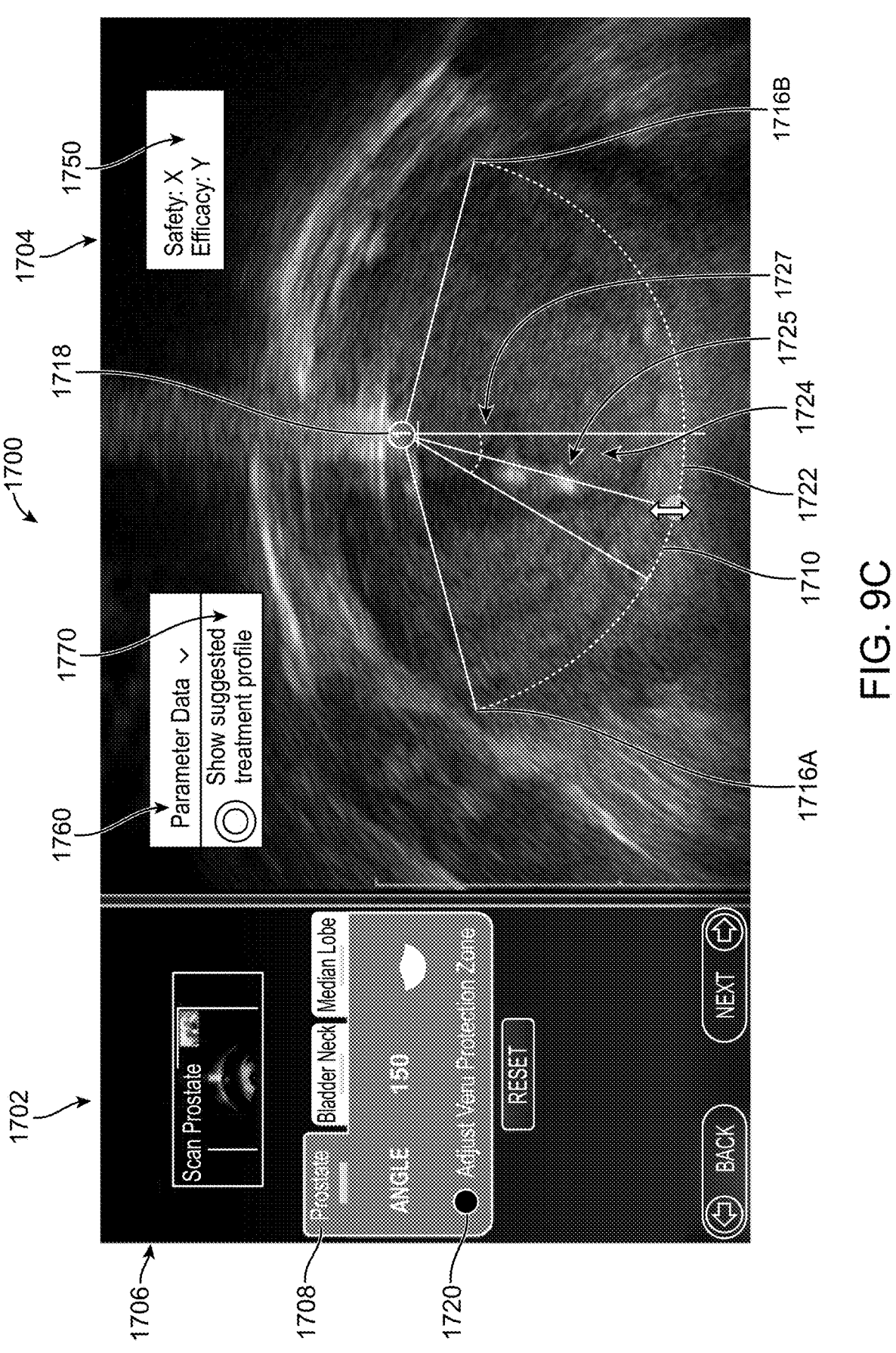
Figure 10:
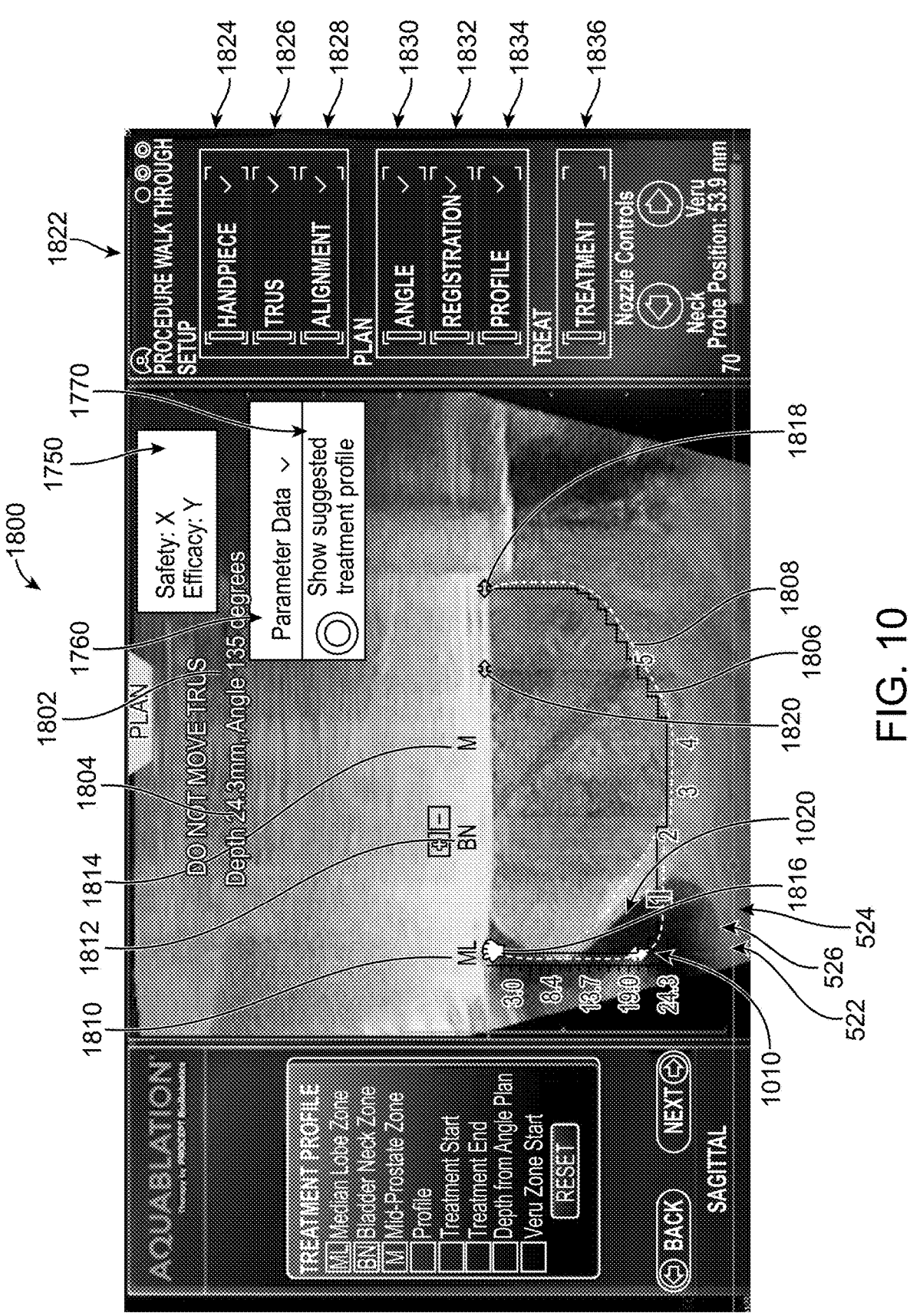
FIG. 10 shows a user interface screen of system with a longitudinal image such as a sagittal image of a tissue and a treatment profile, in accordance with some embodiments.

FIGS. 9A-10 show a user interface that can be used to adjust tissue treatment of a first tissue based on a response of a second tissue to the treatment of the first tissue. The adjustment can be performed by a user, automatically with processor instructions, or a combination thereof, for example with the user confirming a modified treatment plan such as a modified treatment profile overlaid on the image.

FIGS. 9A to 9C show a user interface screen of a system with one or more transverse images of a tissue and a treatment profile.

With reference to FIG. 9A, a user interface 1700 is illustrated that is usable with the devices and methods described herein. The user interface 1700 may comprise two main areas, such as the instruction area 1702 and the control area 1704. The illustrated user interface 1700 layout is exemplary, and any suitable layout or arrangement of information and control inputs can be utilized without departing from the scope hereof.

In the instruction area 1702, a user of the system may be reminded and/or prompted as to the procedural step next in a series of steps. For example, as illustrated, the instruction area 1702 indicates that an imaging device, such as a TRUS probe, is scanning tissue of one or more organs such as the prostate in a scan window 1706. The scan window 1706 may display an area of the anatomy that is being scanned, or that should be scanned for the current procedural step, as will be described hereinafter. The provided view comprises a transverse view of tissue of an organ such as the prostate, although other views such as longitudinal and sagittal views may be displayed as described herein.

An anatomy selection window 1708 provides a user the ability to choose the portion of anatomy for which to establish a treatment profile. As illustrated, the user has selected "Prostate" as the portion of anatomy for which to set a treatment profile.

In some embodiments, a safety and efficacy parameter window 1750 shows values of one or more safety or efficacy parameters as described herein for the subject in response to the resection profiles and ultrasound images. For example, the efficacy values X may comprise one or more of a target efficacy value or an efficacy value determined in response to the resection profile and structures of the image. For example, the window 1750 may display a target efficacy value determined for the patient in consultation with the patient, and a predicted efficacy value generated in response to the resection profile and the image. The window 1750 may display a target safety value determined for the patient in consultation with the patient, and a predicted safety value generated in response to the resection profile and the image. These values can be determined in real time in response to the treatment profiles such as resection profiles shown on the display and structure of the images such as ultrasound images. The safety parameter may comprise a value X, and the efficacy parameter may comprise a value Y.

As the user adjusts the resection profiles, the values of X and Y shown on the display can change. The processor can be configured with instructions to generate an initial resection profile in response to the ultrasound images and the targeted safety and efficacy values that may have been previously agreed upon by the patient and physician. This initial resection profile can be provided on the display and adjusted by the user.

As the portion of anatomy is selected, an image may be displayed that corresponds to the selected portion of anatomy. For example, a real-time image may be displayed
that is captured by an in situ imaging system. In some
instances, a TRUS probe will be placed in proximity to a
patient's prostate and will provide real-time imaging of the
area. In the control area 1704 of the user interface 1700, a
user will be able to specify an area to be treated. The system
is programmed with defaults that aid a user in selecting an
appropriate treatment plan. For example, where the user has
selected the prostate, as illustrated, the control window 1704
initially displays an arc 1710 having an angle 1712 and a
radius 1714. The arc 1710 defines a tissue resection profile,
in which an area of treatment within the arc 1710 is treated
and the area outside the arc 1710 is excluded from treatment.
Arc control handles 1716*a*, 1716*b* are provided and allow a
user to control each leg of the arc 1710 to adjust the angle
1712. A display shows the selected angle 1712 and can be
used to precisely adjust the angle 1712 to define an appro-
priate treatment area. The resection profile shown on the
display initially may comprise a profile determined in
response to desired safety and efficacy values. A vertex 1718
of the arc 1710 shows the placement of a treatment probe.
In some cases, a treatment probe provides for energy deliv-
ery to treat the affected area. In some cases, the treatment
probe is rotated about its longitudinal axis in order to direct
the treatment energy as described herein. Accordingly, the
treatment area will resemble an arc 1710 having a radius
1714 commensurate with the energy intensity. As the arc
control handles 1716A,B are adjusted to define the tissue
resection profile and the treatment area, the settings are
stored for later use during the procedure and to control the
degrees of rotation of the treatment probe during the resec-
tion with energy delivery.

The user interface 1700 may comprise a user input 1760
for the user to select parameters of the model used to
determine the values of the one or more of the safety and
efficacy parameters as disclosed herein. This selection of the
parameters can allow the user to pick parameters that may be
more helpful than others, and to remove parameters that may
be less helpful than others for a particular patient. For
example, if a user believes that a parameter such as age is
less helpful for predicting outcomes, the user can deselect
that parameter as input to the classifier model used to predict
the outcome. Alternatively, if the user believes that age is a
helpful parameter, the user can select age as a parameter to
be used as input to the classifier model.

The user interface 1700 may comprise a user input 1770
for the user to select data to be shown on the display. The
data shown on the display may comprise visualization data
for example. In some embodiments, the user can select
whether to show a suggested treatment profile on the display
overlaid with the planned treatment profile the patient after
user adjustment. This can be helpful to the user to determine
how far the planned treatment profile for the patient deviates
from the profile suggested by the algorithm. The user can
select additional types of visualization data to be shown on
the display. For example, the user can select a planned
trajectory of the energy source for the treatment.

With reference to FIG. 9B, the user interface 1700 shows
that a different portion of anatomy has been selected in the
anatomy selection window 1708 within the instruction area
1702. In some embodiments, the different portion of the
anatomy corresponds to a different transverse image location
along a longitudinal image or sagittal image as described
herein. As shown, the Median Lobe has been selected as the
treatment area within the anatomy selection window 1708
and the control area 1704 has been updated to show imaging
such as one or more transverse images associated with the Median Lobe anatomy. In some embodiments, the one or
more images comprise a series of transverse images, such as
a series of real time images. As before, the control area 1704
overlays a display of the resection profile defined with the
treatment boundary comprising an arc 1710. The arc 1710 is
customizable by a user to manipulate the arc control handles
1716 A, B and in some instances, by specifying the radius
1714. The arc 1710 defines resection profile and the area of
treatment and can provide different resection profiles and
treatment areas for different anatomical areas. For instance,
as shown, the instruction area 1702 allows a user to select
between the Prostate, the Bladder Neck, and the Median
Lobe within the anatomy selection window 1708. In some
embodiments, a transverse ultrasound image is provided at
for each location corresponding to the selected tissue. The
window 1750 can display the safety parameter X and the
efficacy parameter Y, and these values can change in real
time as the user adjusts the resection profile, for example.

Similar to the Prostate setup, when the Median Lobe
anatomy is selected, an image of the treatment area is shown
within the control area 1704, such as by a TRUS probe
properly located to image the anatomical feature of interest,
and a user is able to specify a treatment area for this
anatomical feature. The plurality of resection profiles and
corresponding treatment areas established by the user can be
input into a user interface provided by a computer which
may save the treatment plans for execution by a surgeon,
either with human manipulation of the energy source or
automated movement of the energy source under processor
control with one or more linkages in accordance with the
treatment profiles as described herein.

In some embodiments, the processor is configured with
instructions to adjust the treatment profile based on a
response of a second tissue to the treatment of the first tissue.
In some embodiments, the arc 1710 is adjusted in response
to image treatment data of the second tissue, such as the
trigone of the bladder. For example the arc can be decreased
if the image data during treatment indicates that the second
tissue is receiving greater amounts of energy from the
treatment of the first tissue than would be helpful. Alterna-
tively or in combination, radial distance of the treatment
profile from vertex 1718 can be adjusted, for example
decreased in response to the image data from the second
tissue such as the trigone indicating that the second tissue
has received greater amounts of energy from the treatment
of the first tissue than would be helpful. Although these
adjustments can be performed manually by the user, in some
embodiments the processor is configured with instructions to
output an adjusted profile. The adjusted profile may be
overlaid on the screen for the user to receive and accept or
adjust the adjusted treatment profile with user input as
described herein.

With reference to FIG. 9C, the user interface 1700 is
shown. As illustrated, in the anatomy selection widow 1708,
the Prostate is selected and the control area 1704 shows
real-time imaging data of the selected anatomy. The
anatomy selection window 1708 further has been updated to
select the option labeled "Adjust Veru Protection Zone"
1720. This refers to a treatment plan designed to protect the
verumontanum ("veru") from aggressive resection. The veru
protection zone can be configured in many ways, and may
comprise a butterfly cut profile, for example. In some
embodiments, the treatment profile is configured not to
resect tissue at angles corresponding to the veru protection
zone so as to define the butterfly cut. Although reference is
made to a veru protection zone, the protection zone may
comprise one or more protection zones to protect a delicate tissue structures of a second tissue as described herein, such as a tumor or retina of an eye, for example. In some embodiments, the verumontanum 1725 is visible in the transverse image. In some embodiments, the verumontanum is identified with one or more image processing algorithms of an artificial intelligence algorithm as described herein, such as a convolutional neural network, for example.

As shown, once the "Adjust Very Protection Zone" 1720 radio button has been selected, a new overlay appears over the control area 1704 and defines a veru arc 1722, which is a portion of the arc 1710. The veru arc 1722 shares the vertex 1718 and may share the radius 1714 length with the arc 1710. In some embodiments, the radius of the arc 1722 is adjusted by the user to decrease the radius of the treatment depth such as a resection depth in order to decrease the possibility of damage to the verumontanum. For example, the depth of treatment of a first tissue prostate tissue such as benign prostate hyperplasia tissue can be adjusted to decrease the possibility of damage to a second tissue such as the verumontanum ("veru"). In some embodiments, the depth of penetration of the tissue resection profile corresponds to a resection depth of substantially zero within the veru protection zone, although any suitable radial depth from the energy source near vertex can be used. In some embodiments the user adjusts the depth of penetration along arc 1722 to a second location 1727 with a decreased depth to decrease the possibility of potential damage to the veru. In some embodiments, the radial distance from the vertex 1718 to the second location 1727 is automatically adjusted. In some embodiments, the distance is adjusted during treatment, for example automatically or manually, in response to image data of the verumontanum while tissue at another location is treated as described herein.

The veru arc 1722 comprises a treatment profile that defines an area that is associated with a veru protection zone 1724. In prostate surgery, there can be a risk/reward tradeoff between the efficacy of the procedure and male sexual function as described herein. The aggressiveness of the prostate resection treatment is related to proximity to the verumontanum. If tissue is resected closer to the verumontanum, the effectiveness of the prostate treatment for benign prostatic hyperplasia can increase. However, the risk of male sexual dysfunction may also increase. The window 1750 providing safety and efficacy parameters can be helpful to the user to adjust the treatment profile for the patient to correspond to the targeted safety and efficacy metrics. Similar metrics and adjustments for other tissues as described herein can be provided, such as metrics for the trigone region of the bladder and urinary function.

In some embodiments, the verumontanum is an anatomical landmark near the entrance of the ejaculatory ducts into the urethra and may also be referred to as the seminal colliculus. The structure of the verumontanum consists of striated muscle fibers of the external sphincter, interwoven with smooth muscle tissue from the urethral wall. Some of the described embodiments herein allow for a targeted specific treatment of the prostatic tissue in close proximity to the verumontanum. According to the embodiments illustrated in FIGS. 9A-9C, a user can specify the resection profile a treatment plan for various areas of the first tissue of a first organ such as the prostate. For example, a treatment plan can be created that includes unique treatments and treatment profiles for each of the prostate, bladder neck, and median lobe, and a unique plan and profile for the verumontanum area. In some embodiments, a unique treatment plan and treatment profile are developed for median lobe of the prostate having an intravesical prostatic protrusion and trigone region of the bladder, for example with a transverse image. The treatment profile of the first tissue such as the median lobe of the prostate can be adjusted in response to image data from one or more images of a second tissue, such as an image of one or more of the verumontanum or the prostate.

The user can adjust the resection profiles in response to the safety and efficacy parameters shown on the display.

Although FIGS. 9A to 9C refer to a display coupled to a surgical system, in some embodiments similar images and user input can be used for remote treatment planning and preplanning at a remote location away from the surgical instrument, such as in another room or building, which can be in another state or country, for example. The processor can be configured with instructions for the user to plan the treatment, these parameters can be stored and loaded onto the processor of the surgical system. For example, a diagnostic image of the patient can be generated prior to treatment, for example in an imaging lab. The image can be shown on a display to the user on a mobile device, and the user can adjust the treatment profiles and other aspects of the treatment. Once accepted, the treatment parameters, e.g. the resection profile, can be loaded onto the surgical instrument.

FIG. 10 shows a user interface screen of system with a longitudinal (e.g. sagittal) image of a tissue and a treatment profile. In some embodiments, a user interface 1800 shows a longitudinal (e.g. sagittal) view of the treatment area with the anatomically distal organs to the left of the figure. The user interface may comprise transverse interface 1700 and longitudinal (e.g. sagittal) interface 1800 to plan the treatment profile in three dimensions for 3D volumetric tissue removal. This screen displays information from the treatment plan already entered, such as the angle of rotation of the treatment probe 1802, which is 135 degrees in this example, and the depth of resection 1804, which is 24.3 mm in the illustrated example, although any suitable values may be used.

The user interface 1800 allows further refining of the treatment plan by manipulating a treatment profile 1806. The treatment profile 1806 generally follows an anatomical curve fit 1808 of the area of interest. In some cases, the system can detect the anatomical features, such as through one or more algorithms executed on ultrasound imaging, such as image analysis, feature recognition, edge detection, or some other algorithm or combinations of algorithms to detect a recommended boundary of the anatomical features and/or a recommended boundary of the resection profile and treatment area.

The system can present an overlay of information over the ultrasound imaging information, which may include anatomical portions of organs, instructions, resection profiles, as well as other information. In the illustrated user interface 1800, the overlay identifies areas corresponding to the median lobe zone 1810, the Bladder Neck Zone 1812, and the Mid-Prostate Zone 1814. Each of these identified zones may have a different treatment plan associated therewith. For example, the median lobe zone 1810 may have a designated angle of resection, depth of resection, and translational distance of tissue resection, which may be different than the treatment plan specific to the bladder neck zone 1812, which may also be different than the treatment plan for the mid-prostate zone 1814.

The processor can be configured to not only recognize tissue structures of the various anatomical zones, but also to store information regarding the recommended and chosen treatment plan for each of the zones. For example, information from prior surgeries may be stored in a database that corresponds with one or more treatment plans for individual organs, or portions of individual organs. This information from prior surgeries can be used to train a classifier or a neural network as described herein. The trained classifier or neural network can generate an appropriate recommended treatment plan comprising a plurality of tissue resection profiles. This recommended resection profile can be generated and presented on a display along with the predicted safety value X and predicted safety value Y in window 1750. As a treatment plan comprising a plurality of cut profiles is modified by the user, the processor may receive the modified treatment plan, cut profile and ultrasound images and the trained classifier or neural network can be used to generate updated safety and efficacy parameters shown on display 1750. The trained classifier or neural network may also receive as input patient information, such as age, height, weight, symptoms, and other information as described herein in determining values of the safety and efficacy parameters and in generating a treatment plan.

The user interface 1800 may include controls to allow a user to adjust the treatment plan. For example, a treatment start control 1816, a treatment end control 1818, and a veru zone start control 1820. Any of these controls may be manipulated by a user in order to modify the resection profile of the treatment plan. For example, a user may move one or more of the controls to modify the resection profile, such as by modifying the depth of resection, the location of the resection start control 1816, or the location of the veru start zone control 1820. Changes made by the user at the user interface 1800 are stored in memory of an associated computing system for later or concurrent execution during the procedure. In some cases, the procedure is performed by robotic equipment executing the procedure according to the resection boundary limits.

The user interface 1800 further has informational and/or educational components, such as a procedure walk through area 1822 that provides guidance to a user of the system. For example, as illustrated, the procedure walk through area 1822 includes a list of procedural setup steps for a user to perform, such as locating the handpiece 1824, locating the TRUS probe 1826, and aligning the handpiece and TRUS probe 1826.

The procedure walk through area further includes creation and/or modification of the treatment plan, such as by providing the user and opportunity to enter and/or modify the angle of resection 1830, the registration of the treatment probe 1832, and a cutting profile 1834.

As shown in FIG. 10, the setup steps have been completed for a procedure, as indicated by the checkmarks next to the handpiece 1824, TRUS 1826, alignment 1828, angle 1830, and registration 1832. At the current stage in the illustrated example, a user still should complete the profile 1834 adjustment. Upon completion of the setup steps and plan steps in the user interface 1800, a user can indicate that the procedure is ready to begin by selecting the Treatment icon 1836, at which point, the system may autonomously begin the procedure according to the treatment plan.

Once the treatment has been initiated with the treatment profile, the user may perform additional adjustments to the treatment profile based on the response of the second tissue to treatment of the first tissue as described herein. In some embodiments, the user adjusts the treatment profile from a first treatment profile to a second treatment profile with one or more controls of the user interface. For example, the first treatment profile 1010 can be adjusted to a second treatment profile 1020, and the patient subsequently treated with the second treatment profile 1020. In some embodiments, the treatment profile of the first tissue such as the median lobe of the prostate is adjusted with respect to the second tissue such as the wall 522 of the bladder and trigone tissue 525, although the adjustment may be made with respect to any first tissue and second tissue as described herein. In some embodiments, the treatment profile is adjusted with respect to a profile 526, such as a profile of the inner bladder wall.

In some embodiments, the first treatment profile comprises a first closest distance to the second tissue, in which the first closest distance defines a first gap between the first treatment profile and the second tissue, and the second treatment profile comprises a second closest distance to the second tissue, in which the second closest distance defines a second gap between the second treatment profile and the second tissue.

The first gap may have different length from the second gap, for example. Referring again to the example shown in FIG. 10, the first treatment profile 1010 may define a first closest distance to the trigone tissue 524, and the second treatment profile 1020 may 1020 may define a second closest distance to the trigone tissue 524, in which the second distance is greater than the first distance. By adjusting the gap distance the effect of the treatment of the first tissue on the second tissue can be adjusted as appropriate. While reference is made to the adjustment being performed on a user interface, in some embodiments the adjustment is made automatically by the processor with appropriate instructions, for example. In some embodiments, the second profile is presented to the user on the display of the user interface for acceptance and modification. The user has the option of accepting processor generated second profile as presented initially or modifying the presented second profile and then accepting the profile as modified by the user.

Although reference is made to treatment planning with images and adjusting the treatment profile based on images, other approaches be used. In some embodiments, one or more tissue markers can be mapped with another device such as an endoscope or tissue sensors configured to detect anatomical structures or tissue transitions, for example. Based on reference anatomical data, the location of the second tissue can be determined based on the location of the reference anatomical marker. In some embodiments, one or more visual markers are identified with an endoscope and the treatment plan adjusted by the user in response to the one or more visual markers. The location of the visual marker can be used to estimate the location of a second tissue such as the trigone tissue. In some embodiments, the external sphincter of the urethra is visible from an endoscope image, and the position of the second tissue such as the trigon estimated from the location of the visual marker such as external sphincter. In some embodiments, the tissue marker comprises a bladder opening to the urethra, which can be seen with an endoscope for example. Although reference is made to determining the location of the bladder opening to the urethra with an endoscope, other methods and apparatus can be used. In some embodiments, the opening of the urethra to the bladder is measured with one or more of optical measurements, ultrasound, or electrical impedance measurements for example. In some embodiments, the marker is measured with an impedance probe comprises two or more electrodes, in which the position of the marker corresponds to a change in impedance for example. In some embodiments, when the probe passes from the urethra to the opening of the bladder, there is less tissue engaging the electrodes in the opening to the bladder, such that the impedance changes.

In some embodiments, the handpiece comprises one or more markers, such as depth markers, to indicate the location of the energy source or the tissue mapping probe. In some embodiments, this information of the depth of the energy source can be used with other data to determine when the energy source is near the second tissue such as the trigone. In some embodiments, the handpiece is configured to move the tissue mapping probe with a calibrated translation to determine the depth of the tissue marker to estimate the location of the second tissue, for example.

The treatment profile can also be adjusted in response to a tumor such as cancerous tissue such as a tumor. Work in relation to the present disclosure suggests that approximately 80% of prostate cancer cases have cancer in a peripheral zone of the prostate and approximately 20% of prostate cancer cases have cancer located in a transition zone of the prostate. The treatment profiles as described herein can be adjusted in response to a shape profile of a tumor, for example. In some embodiments, the shape profile is adjusted to selectively treat the cancerous region. Alternatively, the shape profile can be adjusted to decrease interaction of the energy source with the cancerous region.

In some cases, the treatment plan is stored in a database along with other treatment plans and may include data regarding the patient and the treatment plan, such a patient age, weight, height, symptoms, length of symptoms, diagnosis, past treatment history, treatment efficacy, medication history, and the like. Past treatment plans may include data such as angle and resection profile for a plurality of historical treatments for multiple patients and be stored as historical treatment plan data.

The historical treatment plan data may be analyzed by one or more suitable algorithms as described herein, such as one or more of artificial intelligence algorithms, supervised machine learning, unsupervised machine learning, neural networks, or convolutional neural networks. In some cases, the historical treatment plan data is analyzed by one or more machine learning algorithms and may be used to train a classifier. For example, a neural network may analyze the historical treatment data to provide a recommended treatment plan for one or more current patients. For example, based upon the historical treatment data, a neural network may be used to build, train, and deploy a machine learning model including preparing and labeling historical treatment data, choose an algorithm, train the model, validate the model, tune and optimize the model, deploy the model, make predictions about future treatment plans, and provide treatment plans for current or future patients.

In some instances, an artificial intelligence algorithm such as a convolutional neural network may be implemented to analyze visual data, such as ultrasonic imaging from a TRUS probe, and provide feedback to feed into a machine learning model. The visual data analysis may include identifying anatomical features, along with relevant position, size, shape, health, and other information.

The processor as described herein can be configured with instructions to provide the user interface, images and windows as described herein, for example with reference to FIGS. 9A to 10. Alternatively or in combination, the processor can be configured with instructions to adjust the treatment profile of the first tissue in response to image data from the second tissue as described herein. In some embodiments, the processor is configured with instructions to overlay a proposed modified treatment profile on the image of the tissue, prompt the user to accept or modify the treatment profile, and then complete the treatment in response to the modified treatment profile.

FIG. 11 shows a method 1100 of treating a first tissue and adjusting the treatment based on a response of a second tissue to the treatment of the first tissue.

At a step 1105, a treatment probe is inserted into the patient to treat first tissue of the patient. In some embodiments, the treatment probe comprises an energy source. The energy source may comprise one or more of an electrode, a loop electrode, a laser source, a mechanical energy source, a mechanical sheer, an ultrasound probe, a cavitating ultrasound probe, a water jet, e.g. a fixed pressure water jet, a plasma source, a steam source, a morcellator, a trans urethral needle, a photo ablation source, a radiation energy source, a microwave energy source or a water jet evacuation source, for example.

At a step 1110, the imaging device is positioned to image the second tissue and the first tissue. The imaging device may comprise one or more of an ultrasound transducer array, an external ultrasound transducer array, an ultrasound transducer array on the probe comprising the energy source, an ultrasound probe, an elongate ultrasound probe sized for placement in a lumen, a transrectal ultrasound probe, a transvaginal ultrasound probe, magnetic resonance imaging, a magnetic resonance probe, an endoscope or a fluoroscopic imaging device.

At a step 1115, the first tissue and second tissue are imaged, either separately or together, or and combinations thereof. In some embodiments, the image data comprises a series of real time images. While any suitable acquisition and frame rates can be used, in some embodiments the series of real time images comprises a frame rate of at least one hertz and a latency of no more than one second from when an imaging energy is released from the imaging device until an image is shown on the display.

At a step 1120, one or more tissue structures of the first tissue are identified and associated data generated, such as shape data or contrast data. The associated data may comprise any suitable data generated with any suitable algorithm as described herein.

In some embodiments, the anatomical structure of the first tissue structure comprises one or more of a tissue wall, a vesicle, a lumen, a wall of a lumen, a bladder, a wall of a bladder, a neck of a bladder, a wall of a bladder neck, a ureteric orifice, an internal urethral orifice, an external urethral sphincter, a ureter, a wall of a ureter, a prostate, a lobe of a prostate, an intravesical prostatic protrusion, a capsule of a prostate, an internal sphincter, and external sphincter, an artery, a wall of an artery, a vein, a wall of a vein, or a lens of an eye.

At a step 1125, one or more tissue structures of the second the tissue are identified, and associated data generated. The associated data may comprise any suitable data generated with any suitable algorithm as described herein.

In some embodiments, the first tissue comprises a first tissue structure and the second tissue comprises a second tissue structure different from the first tissue structure. The second tissue structure may comprise any suitable tissue, such as one or more connective tissue, muscle tissue, epithelial tissue, muscle tissue, or an anatomical structure associated with a contrast in the image data. In some embodiments, the second tissue structure comprises a second type of tissue adjacent a third type of tissue or a fluid to provide the contrast in the image data from the second tissue structure. The fluid may comprise a liquid such as urine, for example.

In some embodiments, the anatomical structure of the second tissue structure comprises one or more of a tissue wall, a vesicle, a lumen, a wall of a lumen, a bladder, a wall of a bladder, a neck of a bladder, a wall of a bladder neck, a trigone tissue, a ureteric orifice, an internal urethral orifice, an external urethral sphincter, a ureter, a wall of a ureter, a prostate, a lobe of a prostate, an intravesical prostatic protrusion, a capsule of a prostate, a verumontanum of a prostate, an internal sphincter, and external sphincter, an artery, a wall of an artery, a vein, a wall of a vein, a retina of an eye.

In some embodiments, the first tissue comprises tissue of a first organ and the second tissue comprises tissue of a second organ different from the first organ and wherein the processor is configured to process the image data from the tissue of the second organ and output data corresponding to a response of the second tissue to the energy source directed to the tissue of the first organ.

In some embodiments, the second tissue structure comprises a tissue wall facing toward the first tissue structure and wherein the one or more of the treatment profile, the movement of the energy source or the energy source is adjusted in response to the image data from the tissue wall. The image data from the tissue wall may comprises one or more of a shape profile of the tissue wall, a contrast of the tissue wall, a blurring of the tissue wall, a movement of the tissue wall, a deflection of the tissue wall, or a distortion of the tissue wall, for example.

At a step 1130, the three dimensional treatment profile is generated. The three dimensional treatment profile may comprise a three dimensional treatment profile with associated transverse and longitudinal (e.g. sagittal) images as described herein, for example. The transverse and longitudinal (e.g. sagittal) images can be generated by the user manipulating the imaging probe such as an ultrasound probe and capturing transverse images at appropriate locations corresponding to anatomical structures as described herein. Alternatively or in combination, the associated transverse and longitudinal (e.g. sagittal) images may comprise 3D images such as 3D images from a 3D ultrasound probe or other 3D imaging device configured to generate transverse images at predetermined distances along the tissue. In some embodiments the 3D image comprises a tomographic image.

In some embodiments, corresponding movements of the energy source and amounts of energy from the energy source are determined to treat tissue in accordance with the treatment profile, for example to resect tissue to the treatment profile as described herein. The energy source can be configured with one or more of an amount of energy, a power, an irradiance profile, a flow rate, or a pressure, for example. The movement of the probe can be configured to provide corresponding rotational and translational movement such as velocities to treat the tissue in accordance with the treatment profile, for example to resect the tissue to the depth of the treatment profile.

At a step 1135, the three dimensional profile is output to a display of user interface and overlaid on associated images such as one or more of transverse or longitudinal (e.g. sagittal) images as described herein.

At a step 1140, the three dimensional treatment profile is adjusted in response to user input.

At a step 1145, energy from energy source is directed to the first tissue to treat first tissue. The energy source can be selectively directed to the first tissue and the second tissue with movement of the energy source as described herein, such as one or more of a rotation of the energy source or a translation of the energy source. In some embodiments, the energy from the energy source is scanned across the first tissue a scan rate, and the second tissue moves in accordance with the scan rate. In some embodiments, wherein the scan rate comprises an angular sweep rate and the second tissue moves in accordance with the angular sweep rate, such that the movement of this tissue corresponds to the angular sweep rate. In some embodiments, the energy source comprises a mechanical energy source such as a water jet, and the tissue moves in accordance with the sweep rate of the water jet. While the sweep rate of the energy source may comprise any suitable sweep rate, in some embodiments the sweep rate is within a range from about 1 Hz to about 20 Hz and an angle of each sweep is within a range from about 20 degrees to about 180 degrees.

At a step 1150, the first tissue is imaged while energy source treats the first tissue. In some embodiments, the treatment probe is coupled to a first linkage and the imaging device such as an ultrasound probe is coupled to a second linkage. The energy source is moved in accordance with the treatment profile and the imaging device is moved with the energy source to maintain one or more of the second tissue or the second tissue within a field of view of the imaging device. In some embodiments, the processor is configured to move the imaging device synchronously with the energy source to maintain the second tissue within the field of view of the imaging device. Alternatively, processor can be configured to move the imaging device asynchronously with the energy source to maintain the second tissue within the field of view of the imaging device, for example with a stepped movement of the imaging device. In some embodiments, the image data comprises a plurality of transverse images of the treatment probe, the first tissue, and the second tissue and the imaging device is moved to maintain the energy source, the first tissue and the second tissue within a transverse field of view of the imaging device.

At a step 1155, image data from the image of first tissue is processed. In some embodiments, the target tissue resection profile of the first tissue with is compared with a measured tissue resection profile of the first tissue. A comparison of the target tissue resection profile with the measured tissue resection profile can be output from a software module of a processor to a display of a user interface, for example.

At a step 1160, the second tissue is imaged while energy source treats first tissue.

At a step 1165 the image data from the image of second tissue acquired when first tissue treated is processed.

At a step 1170, a response of second tissue to treatment of first tissue is determined. In some embodiments, the image data from the second tissue structure comprises one or more of a shape profile of the second tissue structure, a contrast of the second tissue structure, a blurring of the second tissue structure, a movement of the second tissue structure, a deflection of the second tissue structure or a distortion of the second tissue structure. In some embodiments, a movement of the second tissue is measured in response to the energy from the energy source and one or more of the energy source, a movement of the energy source, or the treatment profile is adjusted in response to the movement of the second tissue.

In some embodiments, the response of the second tissue to treatment of the first tissue is evaluated with differences between images taken at different times. In some embodiments, the image data from the second tissue structure comprises a first image at a first time and a second image at a second time. The processor is configured to determine, based on the first image and the second image, in response to the energy source directed to the first tissue, which can be evaluated with a change to the one or more the shape profile of the second tissue structure, the contrast of the second tissue structure, the blurring of the second tissue structure, the movement of the second tissue structure, the deflection of the second tissue structure, or the distortion of the second tissue structure, for example.

While any suitable images can be used, in some embodiments the first image comprises a first longitudinal (e.g. sagittal) image and the second image comprises a second longitudinal (e.g. sagittal) image and the probe comprises an elongate probe shown extending along the first longitudinal (e.g. sagittal) image and the second longitudinal (e.g. sagittal) image.

At a step 1175, treatment of first tissue is correlated with movement of second tissue, for example correlated a sweep rate of the energy source directed to the first tissue. In some embodiments, an amount of movement of the second tissue corresponds to the sweep rate and is determined from the images. In some embodiments, the movement of the second tissue is correlated with the angular sweep rate of the energy source in order to determine the effect of the treatment of the first tissue on the second tissue.

At a step 1180, data corresponding to the response of second tissue to treatment of first tissue is output.

At a step 1185, data from second tissue is output to a user interface for evaluation by a user such as a health care professional.

At a step 1190, user input from user interface is received, in which the input is related to second tissue output data, such as output data provided to a display of the user interface. In some embodiments, the processor outputs data to a user interface in response to the image data from the second tissue and receives an input from the user to adjust one or more of a treatment profile, the movement of or the energy from the energy source in response to the input from the user. In some embodiments, a proposed modified treatment profile is generated with the processor and overlaid with one or more image of the tissue as described herein.

At a step 1195, the treatment of first tissue is adjusted based on the response of second tissue to treatment of first tissue. The adjustment may comprise any suitable adjustment as described herein. In some embodiments, the processor is configured to adjust one or more of the energy source or a treatment profile of the first tissue structure in response to the image data from the second tissue structure.

In some embodiments, the processor comprises a component of a feedback loop to adjust one or more of a treatment profile, a movement of the energy source or the energy from the energy source in response to the image data from the second tissue. The processor can be configured to automatically adjust the treatment in real time. Alternatively or in combination, the treatment can be adjusted in response to user inputs.

In some embodiments, the processor automatically adjusts the one or more of the treatment profile, the movement or the energy from the energy source in response to the image data from the second tissue.

While the treatment can be adjusted in many ways, in some embodiments the energy source is adjusted with one or more of a movement, a rotation, a translation, an angular velocity, a translational velocity, an energy from the energy source, a power from the energy source, a pump power, a laser power, or an electrical power.

In some embodiments, the first tissue is treated in accordance with a treatment profile and the treatment profile is adjusted in response to the image data from the second tissue. For example, the first tissue can be treated in accordance with a first treatment profile and the first treatment profile adjusted to generate a second tissue profile in response to the image data from the second tissue.

In some embodiments, processor adjusts the energy source to treat the first tissue with decreased interaction of the energy source with the second tissue in response to the image data from the second tissue. Alternatively or in combination, in some embodiments the processor adjusts the energy source to treat the first tissue with increased interaction of the energy source with the second tissue in response to the image data from the second tissue.

At a step 1199, the first tissue is treated with the adjusted treatment profile.

Although FIG. 11 shows a method 1100 of treating a first tissue and adjusting the treatment based on a response of a second tissue to the treatment of the first tissue in accordance with an embodiment, one of ordinary skill in the art will recognize many adaptations and variations. For example, the steps can be performed in any order and may be performed at least partially simultaneously. Some of the steps can be omitted. Some of the steps can be repeated. Some of the steps can be combined. Some of the steps may comprise sub steps of other steps.

FIG. 12 shows a method 1200 of adjusting a probe placed in a first tissue in response to stretching of a second tissue. In some embodiments, the first tissue comprises a tissue of a first organ and the second tissue comprises a tissue of a second organ, for example.

At a step 1205, image data is acquired from a first tissue of the subject and a second tissue of the subject. The image data may comprise any suitable image data as described herein.

At a step 1210, the probe is placed in the subject to treat a first tissue of the subject. The first tissue may comprise any suitable tissue as described herein. In some embodiments, the probe comprises an energy source as described herein.

At a step 1215, the position of the probe in the first tissue is fixed. In some embodiments, the probe is supported on an arm, and the position of the arm is fixed as described herein.

At a step 1220, image data is acquired from the first tissue of the subject and a second tissue of the subject with the probe placed in the subject to treat the first tissue. The image data may be acquired with the probe position fixed, for example. The image data may comprise any suitable image and tissue structure as described herein and may comprise an image of a wall of the second tissue, for example.

At a step 1230, the image data is processed to identify one or more tissue structures of the second tissue and associated shape data. The one or more tissue structures may comprise any suitable tissue structure as described herein. The associated shape data may comprise any data related to shape as described herein, such as shape profile data, deflection data, or sag height data related to a slope of the tissue, for example.

At a step 1240, the image data is processed to generate data related to tissue stretching of the second tissue. The image data can be processed in any suitable way as described herein, such as with an artificial intelligence algorithm such as a convolutional neural network. In some embodiments, the shape data for the second tissue is compared to reference shape data for the second tissue, such as population reference data. Alternatively or in combination, shape data from a first image of the tissue structure can be compared with shape data from a second image of the tissue structure to determine a change in the shape data. The first image may comprise an image prior to placement of the probe and the second image may comprise an image with a probe placed in the first tissue.

At a step 1250, the data related to tissue stretching is output. The output can be provided to a software module, or to a user interface, for example.

At a step 1260, the data related to tissue stretching is output to a user interface. In some embodiments, the output comprises one or more of an alert, a notification or a message to a user to adjust one or more of an angle, a location, or a pose of the probe.

At a step 1270, a probe movement in the first tissue is determined to decrease stretching of the second tissue. In some embodiments, the movement comprises a direction to decrease stretching of the second tissue and may comprise a movement that moves at least a portion of the probe generally toward the second tissue.

At a step 1275, user input to adjust the probe is received. In some embodiments, a proposed movement is provided to a user interface for the user to confirm, and the probe is moved with a robotic arm as described herein.

At a step 1280, placement of the probe in the first tissue is adjusted to decrease stretching of the second tissue. The adjustment may comprise one or more of a placement, an angle, a location or a six degree of freedom (6 DOF) pose of the probe in response to the data related to the stretching of the probe, for example. The adjustment can be performed with manual manipulation by a user, or with a robotic arm, and combinations thereof, for example. In some embodiments, the processor comprises instructions for a first module to output the data related to the stretching of the second tissue and for a second module to receive the data related to the stretching of the second tissue and adjust the one or more of the angle, the location or the 6 DOF pose of the probe, for example.

At a step 1285, a user input is received to confirm adjustment of the probe in the first tissue. In some embodiments, this is helpful to ensure that the probe has been adjusted appropriately for treatment.

At a step 1290, the first tissue of the patient is treated with the adjusted placement of the probe.

Although FIG. 12 shows a method 1200 of adjusting a probe placed in a first tissue in response to stretching of a second tissue in accordance with an embodiment, one of ordinary skill in the art will recognize many adaptations and variations. For example, the steps can be performed in any order and may be performed at least partially simultaneously. Some of the steps can be omitted. Some of the steps can be repeated. Some of the steps can be combined. Some of the steps may comprise sub steps of other steps.

FIG. 13 shows a method 1300 of measuring forces related to tissue pulling on a probe and adjusting the probe in response to tissue pulling on the probe.

At a step 1305, sensor data is acquired from one or more sensors with the probe position fixed in a free standing configuration. In some embodiments, this comprises a calibration step. In some embodiments, the sensor data has been calibrated previously, for example prior to the probe being placed in the patient.

At a step 1310, the probe is placed in subject to treat a first tissue of the subject.

At a step 1315, the position of the probe in the tissue is fixed. In some embodiments, the position of the probe is fixed to prior to measuring the tissue pulling on the probe.

At a step 1320, sensor data is received sensor from one or more sensors with the probe coupled to the arm in a fixed configuration.

At a step 1330, the sensor data is processed.

At a step 1340, the sensor data is processed to generate data related to the first tissue pulling on the probe.

At a step 1350, the data related to tissue pulling on the probe is output.

At a step 1360, the data related to tissue pulling on the probe is output to a user interface.

At a step 1370, a probe movement is determined to decrease tissue pulling on the probe.

At a step 1375, a user input to adjust the probe is received.

At a step 1380, placement of the probe in the first tissue is adjusted to the force from the first tissue pulling on the probe.

At a step 1385, a user input confirming adjustment of the probe in the first tissue is received.

At a step 1390, the first tissue of the patient is treated with the adjusted placement of the probe.

Although FIG. 13 shows a method 1300 of measuring forces related to tissue pulling on a probe and adjusting the probe in response to tissue pulling on the probe in accordance with an embodiment, one of ordinary skill in the art will recognize many adaptations and variations. For example, the steps can be performed in any order and may be performed at least partially simultaneously. Some of the steps can be omitted. Some of the steps can be repeated. Some of the steps can be combined. Some of the steps may comprise sub steps of other steps.

Any one or more of the steps of the method 1100, the method 1200 and the method 1300 can be combined. A processor as described herein can be configured to perform any one or more of the steps of the method 1100, the method 1200, or the method 1300 with any suitable combination of steps. In some embodiments, sensor data related to the first tissue pulling on the probe is combined with image data from the second tissue, such as data related to stretching of the second tissue for example.

Figure 14:
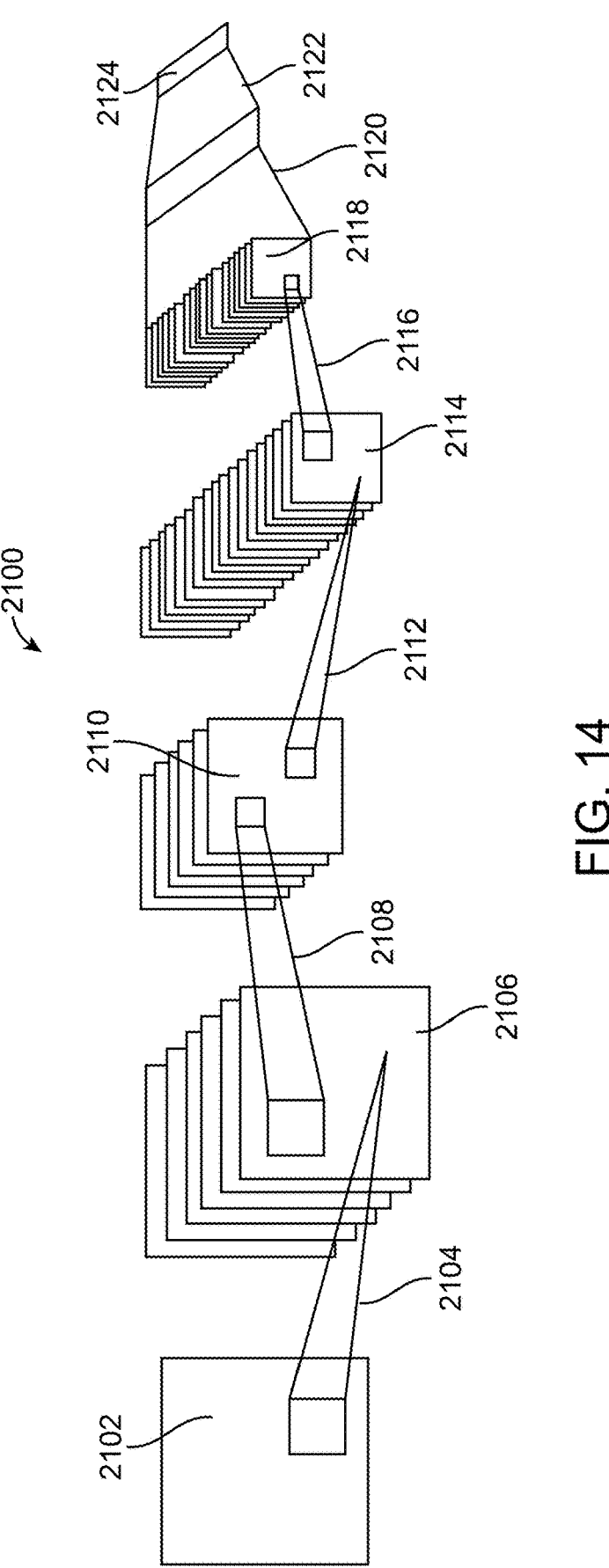
FIG. 14 shows a two-dimensional convolutional neural network, in accordance with some embodiments.

FIG. 14 shows an artificial intelligence ("AI") algorithm suitable for incorporation in accordance with embodiments of the present disclosure. In some embodiments, the artificial intelligence algorithm comprises one or more of image enhancement, image segmentation, a neural network, a convolutional neural network, a transformer, a transformer machine learning model, supervised machine learning, unsupervised machine learning, edge detection, feature recognition, segmentation, 3D model reconstruction, or a multi-modality image fusion, for example.

In some embodiments, the AI algorithm comprises a two-dimensional convolutional neural network (CNN) 2100. In some embodiments, the AI such as a CNN is configured to identify one or more tissue structures of one or more tissue and process the images identify the tissue structure and determine a response of the tissue to treatment. The tissue may comprise a first tissue, or a second tissue, or combinations thereof as described herein. A dataset 2102 is initially provided, which may include imagery from historical treatment data from prior patients and procedures. A convolution operation 2104 results in data in a 2nd data set 2106, which in turn has a pooling layer 2108 applied to result in a pooled layer 2110 of subsample data in order to further condense the spatial size of the representation. The subsample data may be convoluted 2112 to produce a third data set 2114, which may further have a pooling layer applied 2116 to provide subsample data 2118. The subsample data 2118 may be passed through a first fully connected layer 2120 and a second fully connected layer 2122 to generate a classification matrix output 2124. One or more filters can be applied at each convolution layer to provide different types of feature extraction. After the model is defined, it may be compiled and may utilize accuracy of the feature recognition as a performance metric. The model may be trained over time, such as by using historical procedure data as training data and verified according to the model's predictions and verified over time until the model's predictions converge with truth data.

While the trained model can be configured in many ways, in some embodiments the trained model is configured to identify a tissue structure and output one or more metrics associated with the tissue structure, such as one or more of shape data or movement data as described herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising".

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

As used herein, the term "e.g." means for example.

The present disclosure includes the following numbered clauses.

Clause 1. A system for treating tissue of a subject, comprising: a probe comprising an energy source to direct an energy to a first tissue to treat the first tissue; an imaging device configured to acquire image data from the first tissue and a second tissue in proximity to the first tissue; and a processor coupled to the energy source and the imaging device, the processor configured to process the image data from the second tissue and output data corresponding to a response of the second tissue to the energy source directed to the first tissue.

Clause 2. The system of the preceding clause, wherein the processor is configured to adjust one more of a treatment profile, a movement of the energy source, or the energy from the energy source in response to image data from the second tissue.

Clause 3. The system of any of clauses 1 to 2, wherein the processor is configured to automatically adjust the one or more of the treatment profile, the movement or the energy from the energy source in response to the image data from the second tissue.

Clause 4. The system of any of clauses 1 to 3, wherein the processor is configured to output data to a user interface in response to the image data from the second tissue and to receive an input from the user to adjust one or more of a treatment profile, the movement of or the energy from the energy source in response to the input from the user.

Clause 5. The system of any of clauses 1 to 4, wherein the processor comprises a component of a feedback loop to adjust one or more of a treatment profile, a movement of the energy source or the energy from the energy source in response to the image data from the second tissue.

Clause 6. The system of any of clauses 1 to 5, wherein the energy source is adjusted with one or more of a movement, a rotation, a translation, an angular velocity, a translational velocity, an energy from the energy source, a power from the energy source, a pump power, a laser power, or an electrical power.

Clause 7. The system of any of clauses 1 to 6, wherein the processor is configured to adjust the energy source to treat the first tissue with decreased interaction of the energy source with the second tissue in response to the image data from the second tissue.

Clause 8. The system of any of clauses 1 to 7, wherein the processor is configured to adjust the energy source to treat the first tissue with increased interaction of the energy source with the second tissue in response to the image data from the second tissue.

Clause 9. The system of any of clauses 1 to 8, wherein the processor is configured to treat the first tissue in accordance with a treatment profile and adjust the treatment profile in response to the image data from the second tissue.

Clause 10. The system of any of clauses 1 to 9, wherein the processor is configured to treat the first tissue in accordance with a first treatment profile and the first treatment profile is adjusted to generate a second tissue profile in response to the image data from the second tissue.

Clause 11. The system of any of clauses 1 to 10, wherein the first treatment profile comprises a first closest distance to the second tissue, the first closest distance defining a first gap between the first treatment profile and the second tissue and wherein the second treatment profile comprises a second closest distance to the second tissue, the second closest distance defining a second gap between the second treatment profile and the second tissue, the first gap different from the second gap.

Clause 12. The system of any of clauses 1 to 11, wherein the first gap is smaller than the second gap.

Clause 13. The system of any of clauses 1 to 12, wherein the first gap is larger than the second gap.

Clause 14. The system of any of clauses 1 to 13, wherein the first treatment profile comprises a three-dimensional ("3D") treatment profile and the second treatment profile comprises a 3D treatment profile.

Clause 15. The system of any of clauses 1 to 14, wherein the processor is configured to compare a target tissue resection profile of the first tissue with a measured tissue resection profile of the first tissue and output a comparison of the target tissue resection profile with the measured tissue resection profile.

Clause 16. The system of any of clauses 1 to 15, wherein the processor is configured to measure movement of the second tissue in response to the energy from the energy source and adjust one or more of the energy source, a movement of the energy source, or the treatment profile in response to the movement of the second tissue.

Clause 17. The system of any of clauses 1 to 16, wherein the first tissue comprises tissue of a first organ and the second tissue comprises tissue of a second organ different from the first organ and wherein the processor is configured to process the image data from the tissue of the second organ and output data corresponding to a response of the second tissue to the energy source directed to the tissue of the first organ.

Clause 18. The system of any of clauses 1 to 17, wherein first tissue comprises a first tissue structure and the second tissue comprises a second tissue structure different from the first tissue structure and wherein the processor is configured to adjust one or more of the energy source or a treatment profile of the first tissue structure in response to the image data from the second tissue structure.

Clause 19. The system of any of clauses 1 to 18, wherein the image data from the second tissue structure comprises one or more of a shape profile of the second tissue structure, a contrast of the second tissue structure, a blurring of the second tissue structure, a movement of the second tissue structure, a deflection of the second tissue structure or a distortion of the second tissue structure.

Clause 20. The system of any of clauses 1 to 19, wherein the image data from the second tissue structure comprises a first image at a first time and a second image at a second time and the processor is configured to determine, based on the first image and the second image, a change to the one or more the shape profile of the second tissue structure, the contrast of the second tissue structure, the blurring of the second tissue structure, the movement of the second tissue structure, the deflection of the second tissue structure or the distortion of the second tissue structure, in response to the energy source directed to the first tissue.

Clause 21. The system of any of clauses 1 to 20, wherein the second tissue structure comprises one or more connective tissue, muscle tissue, epithelial tissue, muscle tissue, or an anatomical structure associated with a contrast in the image data.

Clause 22. The system of any of clauses 1 to 21, wherein the second tissue structure comprises a second type of tissue adjacent a third type of tissue or a fluid to provide the contrast in the image data from the second tissue structure and optionally wherein the fluid comprises a liquid.

Clause 23. The system of any of clauses 1 to 22, wherein the anatomical structure of the second tissue structure comprises one or more of a tissue wall, a vesicle, a lumen, a wall of a lumen, a bladder, a wall of a bladder, a neck of a bladder, a wall of a bladder neck, a trigone tissue, a ureteric orifice, an internal urethral orifice, an external urethral sphincter, a ureter, a wall of a ureter, a prostate, a lobe of a prostate, an intravesical prostatic protrusion, a capsule of a prostate, a verumontanum of a prostate, an internal sphincter, and external sphincter, an artery, a wall of an artery, a vein, a wall of a vein, a retina of an eye.

Clause 24. The system of any of clauses 1 to 23, wherein an anatomical structure of the first tissue structure comprises one or more of a tissue wall, a vesicle, a lumen, a wall of a lumen, a bladder, a wall of a bladder, a neck of a bladder, a wall of a bladder neck, a ureteric orifice, an internal urethral orifice, an external urethral sphincter, a ureter, a wall of a ureter, a prostate, a lobe of a prostate, an intravesical prostatic protrusion, a capsule of a prostate, an internal sphincter, and external sphincter, an artery, a wall of an artery, a vein, a wall of a vein, a lens of an eye.

Clause 25. The system of any of clauses 1 to 24, wherein the second tissue structure comprises a tissue wall facing toward the first tissue structure and wherein the processor is configured to adjust the one or more of the treatment profile or the energy source in response to the image data from the tissue wall.

Clause 26. The system of any of clauses 1 to 25, wherein the first tissue structure comprises a tissue wall spaced apart from the wall of the second tissue structure with a gap extending therebetween and wherein the processor is configured with instructions to adjust the one or more of the treatment profile or the energy source in response to image data from the wall of the second tissue structure.

Clause 27. The system of any of clauses 1 to 26, wherein the image data from the tissue wall comprises one or more of a shape profile of the tissue wall, a contrast of the tissue wall, a blurring of the tissue wall, a movement of the tissue wall, a deflection of the tissue wall, or a distortion of the tissue wall.

Clause 28. The system of any of clauses 1 to 27, wherein the processor is con1figured to process the image data from one or more of the first tissue or the second tissue with one or more of an artificial intelligence algorithm, image enhancement, image segmentation, a neural network, a convolutional neural network, a transformer, a transformer machine learning model, supervised machine learning, unsupervised machine learning, edge detection, feature recognition, segmentation, 3D model reconstruction, or a multi-modality image fusion.

Clause 29. The system of any of clauses 1 to 28, wherein the energy source comprises one or more of an electrode, a loop electrode, a laser source, a mechanical energy source, a mechanical sheer, an ultrasound probe, a cavitating ultrasound probe, a water jet, e.g. a fixed pressure water jet, a plasma source, a steam source, a morcellator, a trans urethral needle, a photo ablation source, a radiation energy source, a microwave energy source or a water jet evacuation source.

Clause 30. The system of any of clauses 1 to 29, wherein the imaging device comprises one or more of an ultrasound transducer array, an external ultrasound transducer array, an ultrasound transducer array on the probe comprising the energy source, an ultrasound probe, an elongate ultrasound probe sized for placement in a lumen, a transrectal ultrasound probe, a transvaginal ultrasound probe, magnetic resonance imaging, a magnetic resonance probe, an endoscope or a fluoroscopic imaging device.

Clause 31. The system of any of clauses 1 to 30, wherein the image data comprises one or more of longitudinal image data, sagittal image data, transverse image data or 3D ultrasound image data and optionally wherein the image data comprises real time image data.

Clause 32. The system of any of clauses 1 to 31, wherein the image data comprises a first image from a first time and a second image from a second time, the first image and the second imaging showing the probe, the first tissue and the second tissue, and wherein the second tissue moves between the first image and the second image in response to the energy delivered to the first tissue.

Clause 33. The system of any of clauses 1 to 32, wherein the first image comprises a first longitudinal image and the second image comprises a second longitudinal image and the probe comprises an elongate probe shown extending along the first longitudinal image and the second longitudinal image.

Clause 34. The system of any of clauses 1 to 33, wherein the first longitudinal image comprises a first sagittal image and the second longitudinal image comprises a second sagittal image and the elongate probe is shown extending along the first sagittal image and the second sagittal image.

Clause 35. The system of any of clauses 1 to 34, wherein the image data comprises a series of real time images and optionally wherein the series of real time images comprises a frame rate within a range from about 5 Hertz (Hz) to about 250 Hz and a latency from when an imaging energy is released from the imaging device until an image is shown on the display within a range from about 10 milliseconds (ms) to about 1000 ms.

Clause 36. The system of any of clauses 1 to 35, wherein the processor is configured to scan the energy from the energy source across the first tissue a scan rate and the second tissue moves in accordance with the scan rate.

Clause 37. The system of any of clauses 1 to 36, wherein the scan rate comprises an angular sweep rate and the second tissue moves in accordance with the angular sweep rate.

Clause 38. The system of any of clauses 1 to 37, wherein the processor is configured to determine an amount of movement of the second tissue corresponding to the sweep rate and optionally wherein the processor is configured to correlate the movement of the second tissue with the angular sweep rate.

Clause 39. The system of any of clauses 1 to 38, wherein the sweep rate is within a range from about 0.25 Hz to about 30 Hz and an angle of each sweep is within a range from about 10 degrees to about 240 degrees.

Clause 40. The system of any of clauses 1 to 39, wherein the energy source comprises a water jet, the first tissue comprises an intravesical lobe of a prostate extending at least partially into a portion of a bladder, the second tissue comprises trigone tissue and the processor is configured to process the image data from the trigone tissue and output data corresponding to a response of the trigone tissue to the energy directed to the intravesical lobe of the prostate and optionally wherein the lobe comprises a median lobe of the prostate.

Clause 41. The system of any of clauses 1 to 40, further comprising a linkage coupled to the processor and the energy source to move the energy source in accordance with the treatment profile.

Clause 42. The system of any of clauses 1 to 41, wherein the treatment probe is coupled to a first linkage and the ultrasound device is coupled to a second linkage and the processor is configured to move the energy source in accordance with the treatment profile and to move the imaging device with the energy source to maintain the second tissue within a field of view of the imaging device.

Clause 43. The system of any of clauses 1 to 42, wherein the processor is configured to move the imaging device synchronously with the energy source to maintain the second tissue within the field of view of the imaging device.

Clause 44. The system of any of clauses 1 to 43, wherein the image data comprises a plurality of transverse images of the treatment probe, the first tissue, and the second tissue and wherein the processor is configured to move the imaging device to maintain the energy source, the first tissue and the second tissue within a transverse field of view of the imaging device.

Clause 45. A method for treating tissue of a subject, comprising: directing an energy from an energy source to a first tissue to treat the first tissue; acquiring, with an imaging device, image data from the first tissue and a second tissue in proximity to the first tissue; and processing the image data from the second tissue with a processor; and outputting data corresponding to a response of the second tissue to the energy source directed to the first tissue.

Clause 46. The method of clause 45, wherein the processor adjusts one more of a treatment profile, a movement of the energy source, or the energy from the energy source in response to image data from the second tissue.

Clause 47. The method of any of clauses 45 to 46, wherein the processor automatically adjusts the one or more of the treatment profile, the movement or the energy from the energy source in response to the image data from the second tissue.

Clause 48. The method of any of clauses 45 to 47, wherein the processor outputs data to a user interface in response to the image data from the second tissue and receives an input from the user to adjust one or more of a treatment profile, the movement of or the energy from the energy source in response to the input from the user.

Clause 49. The method of any of clauses 45 to 48, wherein the processor comprises a component of a feedback loop to adjust one or more of a treatment profile, a movement of the energy source or the energy from the energy source in response to the image data from the second tissue.

Clause 50. The method of any of clauses 45 to 49, wherein the energy source is adjusted with one or more of a movement, a rotation, a translation, an angular velocity, a translational velocity, an energy from the energy source, a power from the energy source, a pump power, a laser power, or an electrical power.

Clause 51. The method of any of clauses 45 to 50, wherein the processor adjusts the energy source to treat the first tissue with decreased interaction of the energy source with the second tissue in response to the image data from the second tissue.

Clause 52. The method of any of clauses 45 to 51, wherein the processor adjusts the energy source to treat the first tissue with increased interaction of the energy source with the second tissue in response to the image data from the second tissue.

Clause 53. The method of any of clauses 45 to 52, wherein the first tissue is treated in accordance with a treatment profile and the treatment profile is adjusted in response to the image data from the second tissue.

Clause 54. The method of any of clauses 45 to 53, wherein the first tissue is treated in accordance with a first treatment profile and the first treatment profile is adjusted to generate a second tissue profile in response to the image data from the second tissue.

Clause 55. The method of any of clauses 45 to 54, wherein the first treatment profile comprises a first closest distance to the second tissue, the first closest distance defining a first gap between the first treatment profile and the second tissue and wherein the second treatment profile comprises a second closest distance to the second tissue, the second closest distance defining a second gap between the second treatment profile and the second tissue, the first gap different from the second gap.

Clause 56. The method of any of clauses 45 to 55, wherein the first gap is smaller than the second gap.

Clause 57. The method of any of clauses 45 to 56, wherein the first gap is larger than the second gap.

Clause 58. The method of any of clauses 45 to 57, wherein the first treatment profile comprises a three-dimensional ("3D") treatment profile and the second treatment profile comprises a 3D treatment profile.

Clause 59. The method of any of clauses 45 to 58, wherein the processor is configured to compare a target tissue resection profile of the first tissue with a measured tissue resection profile of the first tissue and output a comparison of the target tissue resection profile with the measured tissue resection profile.

Clause 60. The method of any of clauses 45 to 59, wherein movement of the second tissue is measured in response to the energy from the energy source and one or more of the energy source, a movement of the energy source, or the treatment profile is adjusted in response to the movement of the second tissue.

Clause 61. The method of any of clauses 45 to 60, wherein the first tissue comprises tissue of a first organ and the second tissue comprises tissue of a second organ different from the first organ and wherein the processor is configured to process the image data from the tissue of the second organ and output data corresponding to a response of the second tissue to the energy source directed to the tissue of the first organ.

Clause 62. The method of any of clauses 45 to 61, wherein first tissue comprises a first tissue structure and the second tissue comprises a second tissue structure different from the first tissue structure and wherein the processor is configured to adjust one or more of the energy source or a treatment profile of the first tissue structure in response to the image data from the second tissue structure.

Clause 63. The method of any of clauses 45 to 62, wherein the image data from the second tissue structure comprises one or more of a shape profile of the second tissue structure, a contrast of the second tissue structure, a blurring of the second tissue structure, a movement of the second tissue structure, a deflection of the second tissue structure or a distortion of the second tissue structure.

Clause 64. The method of any of clauses 45 to 63, wherein the image data from the second tissue structure comprises a first image at a first time and a second image at a second time and the processor is configured to determine, based on the first image and the second image, a change to the one or more the shape profile of the second tissue structure, the contrast of the second tissue structure, the blurring of the second tissue structure, the movement of the second tissue structure, the deflection of the second tissue structure or the distortion of the second tissue structure, in response to the energy source directed to the first tissue.

Clause 65. The method of any of clauses 45 to 64, wherein the second tissue structure comprises one or more connective tissue, muscle tissue, epithelial tissue, muscle tissue, or an anatomical structure associated with a contrast in the image data.

Clause 66. The method of any of clauses 45 to 65, wherein the second tissue structure comprises a second type of tissue adjacent a third type of tissue or a fluid to provide the contrast in the image data from the second tissue structure and optionally wherein the fluid comprises a liquid.

Clause 67. The method of any of clauses 45 to 66, wherein the anatomical structure of the second tissue structure comprises one or more of a tissue wall, a vesicle, a lumen, a wall of a lumen, a bladder, a wall of a bladder, a neck of a bladder, a wall of a bladder neck, a trigone tissue, a ureteric orifice, an internal urethral orifice, an external urethral sphincter, a ureter, a wall of a ureter, a prostate, a lobe of a prostate, an intravesical prostatic protrusion, a capsule of a prostate, a verumontanum of a prostate, an internal sphincter, and external sphincter, an artery, a wall of an artery, a vein, a wall of a vein, or a retina of an eye.

Clause 68. The method of any of clauses 45 to 67, wherein an anatomical structure of the first tissue structure comprises one or more of a tissue wall, a vesicle, a lumen, a wall of a lumen, a bladder, a wall of a bladder, a neck of a bladder, a wall of a bladder neck, a ureteric orifice, an internal urethral orifice, an external urethral sphincter, a ureter, a wall of a ureter, a prostate, a lobe of a prostate, an intravesical prostatic protrusion, a capsule of a prostate, an internal sphincter, and external sphincter, an artery, a wall of an artery, a vein, a wall of a vein, or a lens of an eye.

Clause 69. The method of any of clauses 45 to 68, wherein the second tissue structure comprises a tissue wall facing toward the first tissue structure and wherein the one or more of the treatment profile, the movement of the energy source or the energy source is adjusted in response to the image data from the tissue wall.

Clause 70. The method of any of clauses 45 to 69, wherein the first tissue structure comprises a tissue wall spaced apart from the wall of the second tissue structure with a gap extending therebetween and wherein the one or more of the treatment profile, the movement of the energy source or the energy source is adjusted in response to image data from the wall of the second tissue structure.

Clause 71. The method of any of clauses 45 to 70, wherein the image data from the tissue wall comprises one or more of a shape profile of the tissue wall, a contrast of the tissue wall, a blurring of the tissue wall, a movement of the tissue wall, a deflection of the tissue wall, or a distortion of the tissue wall.

Clause 72. The method of c any of clauses 45 to 71, wherein the image data from one or more of the first tissue or the second tissue is processed with one or more of an artificial intelligence algorithm, image enhancement, image segmentation, a neural network, a convolutional neural network, a transformer, a transformer machine learning model, supervised machine learning, unsupervised machine learning, edge detection, feature recognition, segmentation, 3D model reconstruction, or a multi-modality image fusion.

Clause 73. The method of any of clauses 45 to 72, wherein the energy source comprises one or more of an electrode, a loop electrode, a laser source, a mechanical energy source, a mechanical sheer, an ultrasound probe, a cavitating ultrasound probe, a water jet, e.g. a fixed pressure water jet, a plasma source, a steam source, a morcellator, a trans urethral needle, a photo ablation source, a radiation energy source, a microwave energy source or a water jet evacuation source.

Clause 74. The method of any of clauses 45 to 73, wherein the imaging device comprises one or more of an ultrasound transducer array, an external ultrasound transducer array, an ultrasound transducer array on the probe comprising the energy source, an ultrasound probe, an elongate ultrasound probe sized for placement in a lumen, a transrectal ultrasound probe, a transvaginal ultrasound probe, magnetic resonance imaging, a magnetic resonance probe, an endoscope or a fluoroscopic imaging device.

Clause 75. The method of any of clauses 45 to 74, wherein the image data comprises one or more of longitudinal image data, sagittal image data, transverse image data or 3D ultrasound image data and optionally wherein the image data comprises real time image data.

Clause 76. The method of any of clauses 45 to 75, wherein the image data comprises a first image from a first time and a second image from a second time, the first image and the second imaging showing the probe, the first tissue and the second tissue, and wherein the second tissue moves between the first image and the second image in response to the energy delivered to the first tissue.

Clause 77. The method of any of clauses 45 to 76, wherein the first image comprises a first longitudinal image and the second image comprises a second longitudinal image and the probe comprises an elongate probe shown extending along the first longitudinal image and the second longitudinal image.

Clause 78. The method of any of clauses 45 to 77, wherein the first longitudinal image comprises a first sagittal image and the second longitudinal image comprises a second sagittal image and the elongate probe is shown extending along the first sagittal image and the second sagittal image.

Clause 79. The method of any of clauses 45 to 78, wherein the image data comprises a series of real time images and optionally wherein the series of real time images comprises a frame rate within a range from about 5 Hertz (Hz) to about 250 Hz and a latency from when an imaging energy is released from the imaging device until an image is shown on the display within a range from about 10 milliseconds (ms) to about 1000 ms.

Clause 80. The method of any of clauses 45 to 79, wherein the energy from the energy source is scanned across the first tissue a scan rate, and the second tissue moves in accordance with the scan rate.

Clause 81. The method of any of clauses 45 to 80, wherein the scan rate comprises an angular sweep rate and the second tissue moves in accordance with the angular sweep rate.

Clause 82. The method of any of clauses 45 to 81, wherein an amount of movement of the second tissue corresponding to the sweep rate is determined and optionally the movement of the second tissue is correlated with the angular sweep rate.

Clause 83. The method of any of clauses 45 to 82, wherein the sweep rate is within a range from about 0.25 Hz to about 30 Hz and an angle of each sweep is within a range from about 10 degrees to about 240 degrees.

Clause 84. The method of any of clauses 45 to 83, wherein the energy source comprises a water jet, the first tissue comprises an intravesical lobe of a prostate extending at least partially into a portion of a bladder, the second tissue comprises trigone tissue and the image data from the trigone tissue is processed and data output from the processed image data, the output data corresponding to a response of the trigone tissue to the energy directed to the intravesical lobe of the prostate and optionally wherein the lobe comprises a median lobe of the prostate.

Clause 85. The method of any of clauses 45 to 84, wherein a linkage coupled to the processor and the energy source moves the energy source in accordance with the treatment profile.

Clause 86. The method of any of clauses 45 to 85, wherein the treatment probe is coupled to a first linkage and the ultrasound device is coupled to a second linkage and the energy source is moved in accordance with the treatment profile and the imaging device is moved with the energy source to maintain the second tissue within a field of view of the imaging device.

Clause 87. The method of any of clauses 45 to 86, wherein the processor is configured to move the imaging device synchronously with the energy source to maintain the second tissue within the field of view of the imaging device.

Clause 88. The method of any of clauses 45 to 87, wherein the image data comprises a plurality of transverse images of the treatment probe, the first tissue, and the second tissue and wherein the imaging device is moved to maintain the energy source, the first tissue and the second tissue within a transverse field of view of the imaging device.

Clause 89. A system for treating a subject, comprising: a probe comprising an energy source to direct an energy to a first tissue to treat the first tissue; an imaging device configured to acquire image data from the first tissue and a second tissue proximate the first tissue; and a processor coupled to the energy source and the imaging device, the processor configured to process the image data from the second tissue and output data related to a stretching of the second tissue in response to placement of the probe.

Clause 90. The system of clause 89, wherein the first tissue comprises a tissue of a first organ and the second tissue comprises a tissue of a second organ.

Clause 91. The system of any of clauses 89 to 90, wherein the processor is configured to output the data related to the stretching of the second tissue to a user interface.

Clause 92. The system of any of clauses 89 to 91, wherein the processor is configured to output one or more of an alert, a notification or a message to a user to adjust one or more of an angle, a location, or a pose of the probe.

Clause 93. The system of any of clauses 89 to 92, wherein the processor is configured to receive an input from the user related to a response of the user to the one or more of the alert, the notification or the message.

Clause 94. The system of any of clauses 89 to 93, wherein the processor is configured to adjust one or more of a placement, an angle, a location or a six degree of freedom (6 DOF) pose of the probe in response to the data related to the stretching of the probe.

Clause 95. The system of any of clauses 89 to 94, further comprising a linkage coupled to the probe and the processor, the linkage configured to adjust the one or more of the placement, the angle, the location, or the 6 DOF pose of the probe.

Clause 96. The system of any of clauses 89 to 95, wherein the linkage comprises a linkage of a robotic arm.

Clause 97. The system of any of clauses 89 to 96, wherein the processor comprises instructions for a first module to output the data related to the stretching of the second tissue and for a second module to receive the data related to the stretching of the second tissue and adjust the one or more of the angle, the location or the 6 DOF pose of the probe.

Clause 98. The system of any of clauses 89 to 97, wherein the processor is configured to output the data related to the stretching of the second tissue to a user interface and receive a user input responsive to the data provided to the user interface, and to adjust the one or more of the placement, the angle, the location or the pose of the probe in response to the user input.

Clause 99. The system of any of clauses 89 to 98, wherein the first tissue comprises tissue of a first organ, and the second tissue comprises tissue of a second organ and wherein the processor is configured to output data corresponding to the stretching of the tissue of the second organ in response to the tissue of the first organ engaging the probe.

Clause 100. The system of any of clauses 89 to 99, wherein the first tissue comprises a first tissue structure detectable in the image data and the processor is configured to identify the first tissue structure and compare profile data of the first tissue structure to reference profile data to determine the stretching of the first tissue.

Clause 101. The system of any of clauses 89 to 100, wherein the reference profile data comprises data from a first image of the tissue prior to placement of the probe.

Clause 102. The system of any of clauses 89 to 101, wherein the first tissue comprises a first tissue structure detectable in the image data and the second tissue comprises a second tissue structure detectable in the image data.

Clause 103. The system of any of clauses 89 to 102, wherein the probe is configured to direct the energy source to the first tissue structure and the processor is configured to identify the second tissue structure and compare profile data of the second tissue structure to reference profile data to determine the stretching of the second tissue.

Clause 104. The system of any of clauses 89 to 103, wherein the reference profile data comprises data from a first image of the tissue prior to placement of the probe.

Clause 105. The system of any of clauses 89 to 104, wherein the second tissue structure comprises a wall and the processor is configured to compare profile data of the wall to reference wall profile data to determine the stretching of the wall.

Clause 106. The system of any of clauses 89 to 105, further comprising one or more sensors coupled to the probe to detect force from the probe engaging the tissue.

Clause 107. The system of any of clauses 89 to 106, wherein the one or more sensors are configured to detect tissue pulling the probe.

Clause 108. The system of any of clauses 89 to 107, wherein the tissue pulling the probe comprises a wall of a lumen.

Clause 109. The system of any of clauses 89 to 108, wherein the wall comprises a urethral wall.

Clause 110. A method of detecting tissue stretching in a subject, comprising: acquiring image data, from an imaging device, of a first tissue and a second tissue proximate the first tissue with a probe placed in the first tissue, the probe comprising an energy source to direct an energy to the first tissue to treat the first tissue; and processing, with a processor, the image data from the second tissue to generate output data related to a stretching of the second tissue in response to placement of the probe in the first tissue.

Clause 111. The method of clause 110, wherein the first tissue comprises a tissue of a first organ and the second tissue comprises a tissue of a second organ.

Clause 112. The method of any of clauses 110 to 111, wherein the processor outputs the data related to the stretching of the second tissue to a user interface.

Clause 113. The method of any of clauses 110 to 112, wherein the processor outputs one or more of an alert, a notification or a message to a user to adjust one or more of an angle, a location, or a pose of the probe.

Clause 114. The method of any of clauses 110 to 113, wherein the processor receives an input from the user related to a response of the user to the one or more of the alert, the notification or the message.

Clause 115. The method of any of clauses 110 to 114, wherein one or more of a placement, an angle, a location or a six degree of freedom (6 DOF) pose of the probe, is adjusted in response to the data related to the stretching of the probe.

Clause 116. The method of any of clauses 110 to 115, further comprising a linkage coupled to the probe and the processor, the linkage configured to adjust the one or more of the placement, the angle, the location, or the 6 DOF pose of the probe.

Clause 117. The method of any of clauses 110 to 116, wherein the linkage comprises a linkage of a robotic arm.

Clause 118. The method of any of clauses 110 to 117, wherein the processor comprises instructions for a first module to output the data related to the stretching of the second tissue and for a second module to receive the data related to the stretching of the second tissue and adjust the one or more of the angle, the location or the 6 DOF pose of the probe.

Clause 119. The method of any of clauses 110 to 118, wherein the processor is configured to output the data related to the stretching of the second tissue to a user interface and receive a user input responsive to the data provided to the user interface, and to adjust the one or more of the placement, the angle, the location or the pose of the probe in response to the user input.

Clause 120. The method of any of clauses 110 to 119, wherein the first tissue comprises tissue of a first organ, and the second tissue comprises tissue of a second organ and wherein the processor is configured to output data corresponding to the stretching of the tissue of the second organ in response to the tissue of the first organ engaging the probe.

Clause 121. The method of any of clauses 110 to 120, wherein the first tissue comprises a first tissue structure detectable in the image data and the processor is configured to identify the first tissue structure and compare profile data of the first tissue structure to reference profile data to determine the stretching of the first tissue.

Clause 122. The method of any of clauses 110 to 121, wherein the reference profile data comprises data from a first image of the tissue prior to placement of the probe.

Clause 123. The method of any of clauses 110 to 122, wherein the first tissue comprises a first tissue structure detectable in the image data and the second tissue comprises a second tissue structure detectable in the image data.

Clause 124. The method of any of clauses 110 to 123, wherein the probe is configured to direct the energy source to the first tissue structure and the processor is configured to identify the second tissue structure and compare profile data of the second tissue structure to reference profile data to determine the stretching of the second tissue.

Clause 125. The method of any of clauses 110 to 124, wherein the reference profile data comprises data from a first image of the tissue prior to placement of the probe.

Clause 126. The method of any of clauses 110 to 125, wherein the second tissue structure comprises a wall and the processor is configured to compare profile data of the wall to reference wall profile data to determine the stretching of the wall.

Clause 127. The method of any of clauses 110 to 126, wherein one or more sensors coupled to the probe detects force from the probe engaging the tissue.

Clause 128. The method of any of clauses 110-127, wherein the one or more sensors detects tissue pulling the probe.

Clause 129. The method of any of clauses 110 to 128, wherein the tissue pulling the probe comprises a wall of a lumen.

Clause 130. The method of any of clauses 110 to 129, wherein the wall comprises a urethral wall.

Clause 131. A system for treating tissue of a subject, comprising: a probe comprising an energy source to direct an energy to the tissue to treat the tissue, the probe sized for insertion into the subject; an arm coupled to the probe to support the probe; one more sensors coupled to the probe to measure a force from the tissue pulling on the probe; a processor coupled to the one or more sensors, the processor configured to output data related to the force from the tissue pulling on the probe to a user interface.

Clause 132. The system of clause 131, wherein the arm and the probe comprise a fixed pose when the sensor measures the force and the processor provides the data.

Clause 133. The system of any of clauses 131 to 132, wherein the arm comprises a robotic arm.

Clause 134. The system of any of clauses 131 to 133, wherein the arm comprises manually movable arm configured to allow a user to move the arm to decrease the force from the tissue pulling on the probe.

Clause 135. The system of any of clauses 131 to 134, wherein the processor is configured to determine a force vector corresponding to a direction of the tissue pulling on the probe.

Clause 136. A method for treating tissue of a subject, comprising: receiving data from one more sensors coupled to a probe to measure a force from the tissue pulling on the probe, wherein the probe comprises an energy source to direct an energy to the tissue to treat the tissue, wherein the probe is supported with an arm with the probe inserted into the subject; processing the sensor data to output data related to the force from the tissue pulling on the probe to a user interface.

Clause 137. The method of clause 136, wherein the arm and the probe comprise fixed pose when the one or more sensors measures the force of the tissue pulling on the probe.

Clause 138. The method of any of clauses 136 to 137, wherein the arm comprises a robotic arm.

Clause 139. The method of any of clauses 136 to 138, wherein the arm comprises manually movable arm configured to allow a user to move the arm to decrease the force from the tissue to the sensor.

Clause 140. The method of any of clauses 136 to 139, wherein the processor is configured to determine a vector corresponding to a direction of the tissue pulling on the probe.

Clause 141. A computer readable medium configured to perform the method of any one of the preceding claims.

Clause 142. A system comprising a processor configured to perform the method of any one of the preceding claims.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A system for treating tissue of a subject, comprising:
   a probe configured to be inserted into a patient and comprising an energy source configured to direct an energy to a first tissue to treat the first tissue;
   an imaging device configured to be inserted into the patient and further configured to acquire image data from the first tissue and a second tissue in proximity to the first tissue; and
   a processor configured to receive data from the energy source and the imaging device, the processor further configured to:
      cause provision on a display of at least one image based on the image data from the first tissue and the second tissue;

cause provision on the display of an overlay on the at least one image, the overlay comprising a treatment profile for treating the first tissue with the energy from the energy source;

process the image data from the second tissue;

determine a response of the second tissue to the energy source directed to the first tissue;

receive a user input with instructions corresponding to an adjusted treatment profile;

adjust the treatment profile based on the user input and determine the adjusted treatment profile based on the response of the second tissue to the energy source directed to the first tissue;

cause provision on the display of a modified overlay on the at least one image, the modified overlay determined based on the adjusted treatment profile;

prompt the user to accept or modify the adjusted treatment profile on the display; and cause the energy source to complete treatment in response to the user accepting or modifying the adjusted treatment profile.

2. The system of claim 1, wherein the processor is configured to adjust one more of the treatment profile, a movement of the energy source or the energy from the energy source in response to image data from the second tissue.

3. The system of claim 2, wherein the processor is configured to automatically adjust the one or more of the treatment profile, the movement or the energy from the energy source in response to the image data from the second tissue.

4. The system of claim 1, wherein the processor is configured to output data to a user interface in response to the image data from the second tissue, receive via the user interface an input from a user to adjust one or more of the treatment profile, a movement of the energy source, or the energy from the energy source, and adjust the one or more of the treatment profile, the movement of or the energy from the energy source in response to the input from the user.

5. The system of claim 1, wherein the processor comprises a component of a feedback loop to adjust one or more of the treatment profile, a movement of the energy source or the energy from the energy source in response to the image data from the second tissue.

6. The system of claim 1, wherein the energy source is adjusted with one or more of a movement, a rotation, a translation, an angular velocity, a translational velocity, an energy from the energy source, a power from the energy source, a pump power, a laser power, or an electrical power.

7. The system of claim 6, wherein the processor is configured to adjust the energy source to treat the first tissue with decreased interaction of the energy source with the second tissue in response to the image data from the second tissue.

8. The system of claim 6, wherein the processor is configured to adjust the energy source to treat the first tissue with increased interaction of the energy source with the second tissue in response to the image data from the second tissue.

9. The system of claim 1, wherein the treatment profile comprises a first closest distance to the second tissue, the first closest distance defining a first gap between the treatment profile and the second tissue and wherein the adjusted treatment profile comprises a second closest distance to the second tissue, the second closest distance defining a second gap between the adjusted treatment profile and the second tissue, the first gap different from the second gap.

10. The system of claim 9, wherein the first gap is smaller than the second gap.

11. The system of claim 9, wherein the first gap is larger than the second gap.

12. The system of claim 1, wherein the treatment profile comprises a three-dimensional ("3D") treatment profile and the adjusted treatment profile comprises a 3D treatment profile.

13. The system of claim 1, wherein the processor is configured to compare a target tissue resection profile of the first tissue with a measured tissue resection profile of the first tissue and output a comparison of the target tissue resection profile with the measured tissue resection profile.

14. The system of claim 1, wherein the processor is configured to measure movement of the second tissue in response to the energy from the energy source and adjust one or more of the energy source, a movement of the energy source, or the treatment profile in response to the movement of the second tissue.

15. The system of claim 1, wherein the first tissue comprises tissue of a first organ and the second tissue comprises tissue of a second organ different from the first organ and wherein the processor is configured to process the image data from the tissue of the second organ and output data corresponding to a response of the second tissue to the energy source directed to the tissue of the first organ.

16. The system of claim 1, wherein first tissue comprises a first tissue structure and the second tissue comprises a second tissue structure different from the first tissue structure and wherein the processor is configured to adjust one or more of the energy source or a treatment profile of the first tissue structure in response to the image data from the second tissue structure.

17. The system of claim 16, wherein the image data from the second tissue structure comprises one or more of a shape profile of the second tissue structure, a contrast of the second tissue structure, a blurring of the second tissue structure, a movement of the second tissue structure, a deflection of the second tissue structure or a distortion of the second tissue structure.

18. The system of claim 17, wherein the image data from the second tissue structure comprises a first image at a first time and a second image at a second time and the processor is configured to determine, based on the first image and the second image, a change to the one or more shape profile of the second tissue structure, the contrast of the second tissue structure, the blurring of the second tissue structure, the movement of the second tissue structure, the deflection of the second tissue structure or the distortion of the second tissue structure, in response to the energy from the energy source directed to the first tissue.

19. The system of claim 1, wherein the energy from the energy source is scanned across the first tissue at a scan rate and the second tissue moves in accordance with the scan rate.

20. The system of claim 19, wherein the scan rate comprises an angular sweep rate and the second tissue moves in accordance with the angular sweep rate, wherein the processor is configured to determine an amount of movement of the second tissue corresponding to the angular sweep rate and wherein the processor is configured to correlate the movement of the second tissue with the angular sweep rate to determine an effect of treatment of the first tissue on the second tissue.

21. The system of claim 1, wherein the treatment profile comprises a first distance to the second tissue along the treatment profile and the adjusted treatment profile comprises a second distance to the second tissue, the first distance being less than the second distance.

\* \* \* \* \*